US012721953B2

(12) United States Patent
Atterbury et al.

(10) Patent No.: US 12,721,953 B2
(45) Date of Patent: Sep. 1, 2026

(54) DEVICES AND PROCESSES FOR DELIVERY OF THERAPEUTIC FLUIDS

(71) Applicant: Eli Lilly and Company, Indianapolis, IN (US)

(72) Inventors: William Godwin Atterbury, Columbus, OH (US); Corrie Jo Bennison, Lewis Center, OH (US); Yelena N. Davis, Worthington, OH (US); David Arthur Holley, Lancaster, OH (US); John Paul Tallarico, Powell, OH (US); Jessica Diane Young, Columbus, OH (US)

(73) Assignee: Eli Lilly and Company, Indianapolis, IN (US)

( * ) Notice: Subject to any disclaimer, the term of this patent is extended or adjusted under 35 U.S.C. 154(b) by 692 days.

(21) Appl. No.: 18/044,597

(22) PCT Filed: Sep. 1, 2021

(86) PCT No.: PCT/US2021/048573
§ 371 (c)(1),
(2) Date: Mar. 9, 2023

(87) PCT Pub. No.: WO2022/055758
PCT Pub. Date: Mar. 17, 2022

(65) Prior Publication Data

US 2024/0009403 A1 Jan. 11, 2024

Related U.S. Application Data

(60) Provisional application No. 63/076,997, filed on Sep. 11, 2020.

(51) Int. Cl.
*A61M 5/32* (2006.01)
*A61M 5/315* (2006.01)

(52) U.S. Cl.
CPC ........ *A61M 5/3234* (2013.01); *A61M 5/3157* (2013.01)

(58) Field of Classification Search
CPC .............. A61M 5/3234; A61M 5/3157; A61M 2005/206; A61M 2005/2073; A61M 5/2033
See application file for complete search history.

(56) References Cited

U.S. PATENT DOCUMENTS 5,405,362 A * 4/1995 Kramer ................ A61M 5/315 600/510
2004/0019326 A1* 1/2004 Gilbert ............... A61M 5/2033 604/135

(Continued)

FOREIGN PATENT DOCUMENTS

EP 2596823 5/2013
WO 2013/119591 8/2013

(Continued)

OTHER PUBLICATIONS

International Search Report of the International Searching Authority pertaining to International Application No. PCT/US2021/048573; Date of Mailing: Dec. 7, 2021; 6 pages.

(Continued)

*Primary Examiner* — Esley G Harris
*Assistant Examiner* — Neeraja Gollamudi
(74) *Attorney, Agent, or Firm* — Jonathan C. Anderson

(57) ABSTRACT

A therapeutic agent delivery system includes a therapeutic agent delivery assembly carried by a housing. The therapeutic agent delivery assembly includes a chamber including a passageway, a therapeutic agent carried in the passageway, and a needle in communication with the passageway. The therapeutic agent delivery assembly is translatable relative to the housing from a stowed configuration to a deployed configuration, and from the deployed configuration to a (Continued)

retracted configuration. The system further includes a user input configured to be actuated by a user, and actuation of the user input translates the therapeutic agent delivery assembly from the stowed configuration to the deployed configuration. The system further includes a retraction mechanism that translates the therapeutic agent delivery assembly from the deployed configuration to the retracted configuration.

12 Claims, 40 Drawing Sheets

(56) References Cited

U.S. PATENT DOCUMENTS

2005/0203461 A1 9/2005 Flaherty
2008/0051711 A1* 2/2008 Mounce .............. A61M 5/1413 604/131
2011/0306929 A1* 12/2011 Levesque .......... A61M 5/14248 604/150
2014/0330216 A1* 11/2014 Weaver ............... A61M 5/3232 29/469
2017/0224915 A1 8/2017 Destefano
2019/0307959 A1 10/2019 Guillermo

FOREIGN PATENT DOCUMENTS

WO 2018/142106 8/2018
WO 2019/023053 1/2019
WO 2019/118261 6/2019
WO 2020/131552 6/2020
WO 2020/131577 6/2020

OTHER PUBLICATIONS

Written Opinion of the International Searching Authority pertaining to International Application No. PCT/US2021/048573; Date of Mailing: Dec. 7, 2021; 11 pages.

* cited by examiner

DEVICES AND PROCESSES FOR DELIVERY OF THERAPEUTIC FLUIDS

FIELD OF THE DISCLOSURE

The present disclosure relates to processes and devices for parenteral delivery of therapeutic agents. More particularly, the present disclosure relates to processes and devices for parenteral delivery of high-viscosity therapeutic fluids (for example, protein therapeutics).

BACKGROUND OF THE DISCLOSURE

Protein therapeutics is an emerging class of drug therapy that provides treatment for a broad range of diseases, such as autoimmune disorders, cardiovascular diseases, diabetes, and cancer. A common delivery method for some protein therapeutics, such as monoclonal antibodies, is through intravenous infusion, in which large volumes of dilute solutions are delivered over time. Intravenous infusion usually requires the supervision of a doctor or nurse and is performed in a clinical setting. This can be inconvenient for a patient, and so efforts are being made to permit the delivery of protein therapeutics at home. Desirably, a protein therapeutic formulation can be administered using a syringe for subcutaneous delivery instead of requiring intravenous administration. Subcutaneous injections are commonly administered by laypersons, for example in the administration of insulin by diabetics.

Transitioning therapeutic protein formulations from intravenous delivery to injection devices like syringes and injection pens requires addressing challenges associated with delivering high concentrations of high molecular weight molecules in a manner that is easy, reliable, and causes minimal pain to the patient. In this regard, while intravenous bags typically have a volume of 1 liter, the standard volume for a syringe ranges from 0.3 milliliters up to 25 milliliters. Thus, depending on the drug, to deliver the same amount of therapeutic proteins, the concentration may have to increase by a factor of 40 or more. Also, injection therapy is moving towards smaller needle diameters and faster delivery times for purposes of patient comfort and compliance.

Delivery of protein therapeutics is also challenging because of the high viscosity associated with such therapeutic formulations, and the high forces needed to push such formulations through a parenteral device. Formulations with absolute viscosities above 40-60 centipoise (cP) may be difficult to deliver by conventional spring driven auto-injectors for multiple reasons. Structurally, the footprint of a spring for the amount of pressure delivered is relatively large and fixed to specific shapes, which reduces flexibility of design for delivery devices. Next, auto-injectors are usually made of plastic parts. However, a large amount of energy must be stored in the spring to reliably deliver high-viscosity fluids. If not properly designed, this stored energy may cause damage to the plastic parts due to creep, which is the tendency of the plastic part to permanently deform under stress. An auto-injector typically operates by using the spring to push a needle-containing internal component towards an outer edge of the housing of the syringe. The sound associated with the operation of a spring-based auto-injector may cause patient anxiety, potentially reducing future compliance. The generated pressure versus time profile of such a spring driven auto-injector cannot be readily modified, which prevents users from fine tuning pressure to meet their delivery needs.

It would be desirable to provide processes and devices by which a therapeutic fluid, in particular a high-viscosity fluid, could be self-administered in a reasonable time and with a limited injection space. These processes and devices could be used to deliver high-concentration protein, high-viscosity pharmaceutical formulations, or other therapeutic fluids.

SUMMARY

According to an embodiment of the present disclosure, a therapeutic agent delivery system includes a housing having a distal end portion. The system further includes a therapeutic agent delivery assembly carried by the housing. The therapeutic agent delivery assembly includes a chamber including a passageway, a therapeutic agent carried in the passageway, and a needle in communication with the passageway. The therapeutic agent delivery assembly is translatable relative to the housing from a stowed configuration to a deployed configuration. In the deployed configuration, the needle at least partially extends distally from the distal end portion of the housing. The therapeutic agent delivery assembly is also translatable relative to the housing from the deployed configuration to a retracted configuration. In the retracted configuration, the needle is disposed proximally relative to the distal end portion of the housing. The system further includes a user input configured to be actuated by a user, and actuation of the user input translates the therapeutic agent delivery assembly from the stowed configuration to the deployed configuration. The system further includes a retraction mechanism. The retraction mechanism includes a biasing element that is reconfigurable from a higher energy storage configuration to a lower energy storage configuration. The retraction mechanism further includes a release device that is coupled to the biasing element. The release device is actuatable to permit the biasing element to reconfigure from the higher energy storage configuration to the lower energy storage configuration, and the biasing element thereby translates the therapeutic agent delivery assembly from the deployed configuration to the retracted configuration.

According to another embodiment of the present disclosure, a therapeutic agent delivery system includes a housing having a distal end portion. The system further includes a therapeutic agent delivery assembly carried by the housing. The therapeutic agent delivery assembly includes a chamber including a passageway, a therapeutic agent carried in the passageway, and a needle in communication with the passageway. The therapeutic agent delivery assembly is translatable relative to the housing from a stowed configuration to a deployed configuration. In the deployed configuration, the needle at least partially extends distally from the distal end portion of the housing. The therapeutic agent delivery assembly is translatable relative to the housing from the deployed configuration to a retracted configuration. In the retracted configuration the needle is disposed proximally relative to the distal end portion of the housing. The system further includes a user input that is configured to be actuated by a user. Actuation of the user input translates the therapeutic agent delivery assembly from the stowed configuration to the deployed configuration. The system further includes an electronics assembly that is configured to send a retraction signal and a retraction mechanism that is operatively coupled to the electronics assembly. The retraction mechanism includes a biasing element that is reconfigurable from a higher energy storage configuration to a lower energy storage configuration upon the retraction mechanism receiving the retraction signal from the electronics assembly. The biasing element thereby translates the therapeutic agent delivery assembly from the deployed configuration to the retracted configuration.

According to yet another embodiment of the present disclosure, a therapeutic agent delivery system includes a housing having a distal end portion. The system further includes a therapeutic agent delivery assembly carried by the housing. The therapeutic agent delivery assembly includes a chamber including a passageway, a therapeutic agent carried in the passageway, and a needle in communication with the passageway. The therapeutic agent delivery assembly is translatable relative to the housing from a stowed configuration to a deployed configuration. In the deployed configuration, the needle at least partially extends distally from the distal end portion of the housing. The therapeutic agent delivery assembly is translatable relative to the housing from the deployed configuration to a retracted configuration. In the retracted configuration, the needle is disposed proximally relative to the distal end portion of the housing. The system further includes a user input that is configured to be actuated by a user, and actuation of the user input translates the therapeutic agent delivery assembly from the stowed configuration to the deployed configuration. The system further includes a retraction mechanism, and the retraction mechanism includes a biasing element that is reconfigurable from a higher energy storage configuration to a lower energy storage configuration. The retraction mechanism has a locked configuration and an unlocked configuration.

BRIEF DESCRIPTION OF THE DRAWINGS

The above-mentioned and other features and advantages of this disclosure, and the manner of attaining them, will become more apparent and will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

The present disclosure relates to systems, devices, and processes for parenteral delivery of therapeutic agents, such as high-viscosity therapeutic fluids. Such systems and devices are illustratively provided with relatively compact profiles.

1. Drugs/Therapeutic Agents

Systems and devices according to the present disclosure may carry and facilitate delivery of a drug to a subject. The term "drug" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, combined GIP/GLP-1 agonists such as tirzepatide, oxyntomodulin analogs, oxyntomodulin derivatives, therapeutic antibodies and any therapeutic agent that is capable of delivery by devices according to the present disclosure. The drug may be formulated with one or more excipients. Devices according to the present disclosure are operated in a manner generally as described herein by a patient, caregiver or healthcare professional to deliver a drug to a subject.

In certain embodiments, a therapeutic agent is protein, such as a monoclonal antibody or some other protein which is therapeutically useful. In some embodiments, the protein may have a concentration of from about 75 mg/mL to about 500 mg/mL in a fluid. In certain embodiments, the protein may have a concentration of about 150 mg/mL, 200 mg/mL, 250 mg/mL, or more. A drug may further contain a solvent or non-solvent, such as water, perfluoroalkane solvent, safflower oil, or benzyl benzoate.

A drug may be a fluid, more specifically a high-viscosity fluid and may have an absolute viscosity of from about 5 cP to about 1000 cP. In certain embodiments, a high-viscosity fluid has an absolute viscosity of at least about 10 cP, 20 cP, 30 cP, 40 cP, 50 cP, 60 cP, or more.

2. Therapeutic Agent Delivery System

Figure 1:
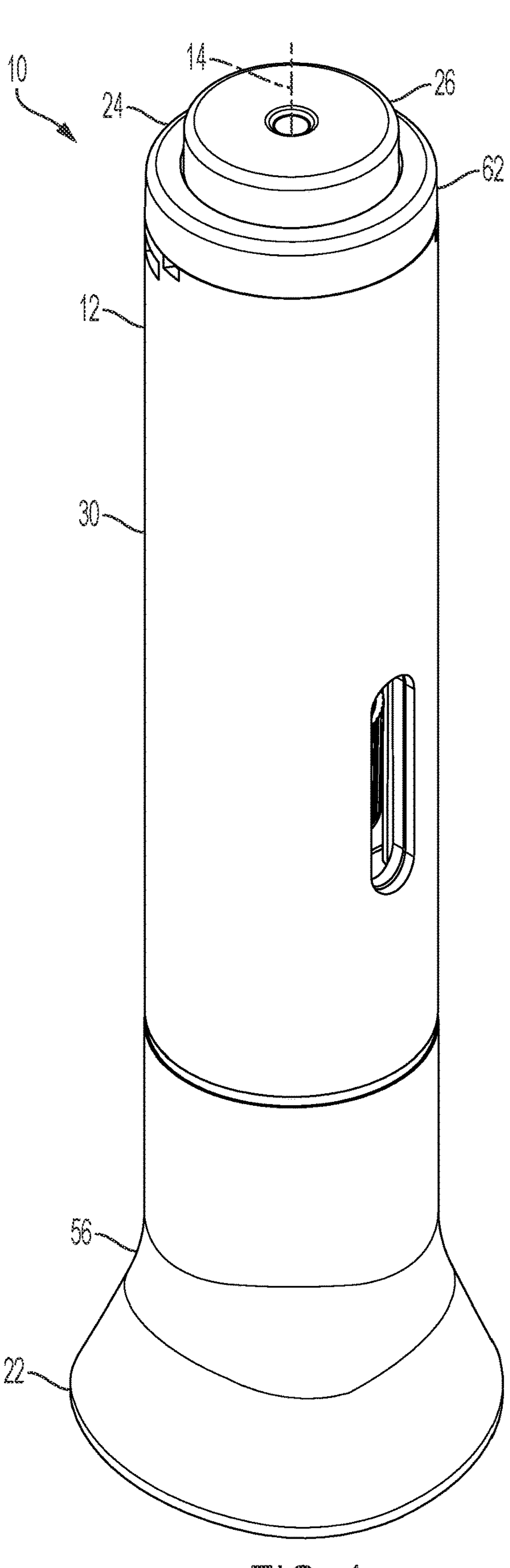
FIG. 1 is a top perspective view of a therapeutic agent delivery system according to an embodiment of the present disclosure.
Figure 2:
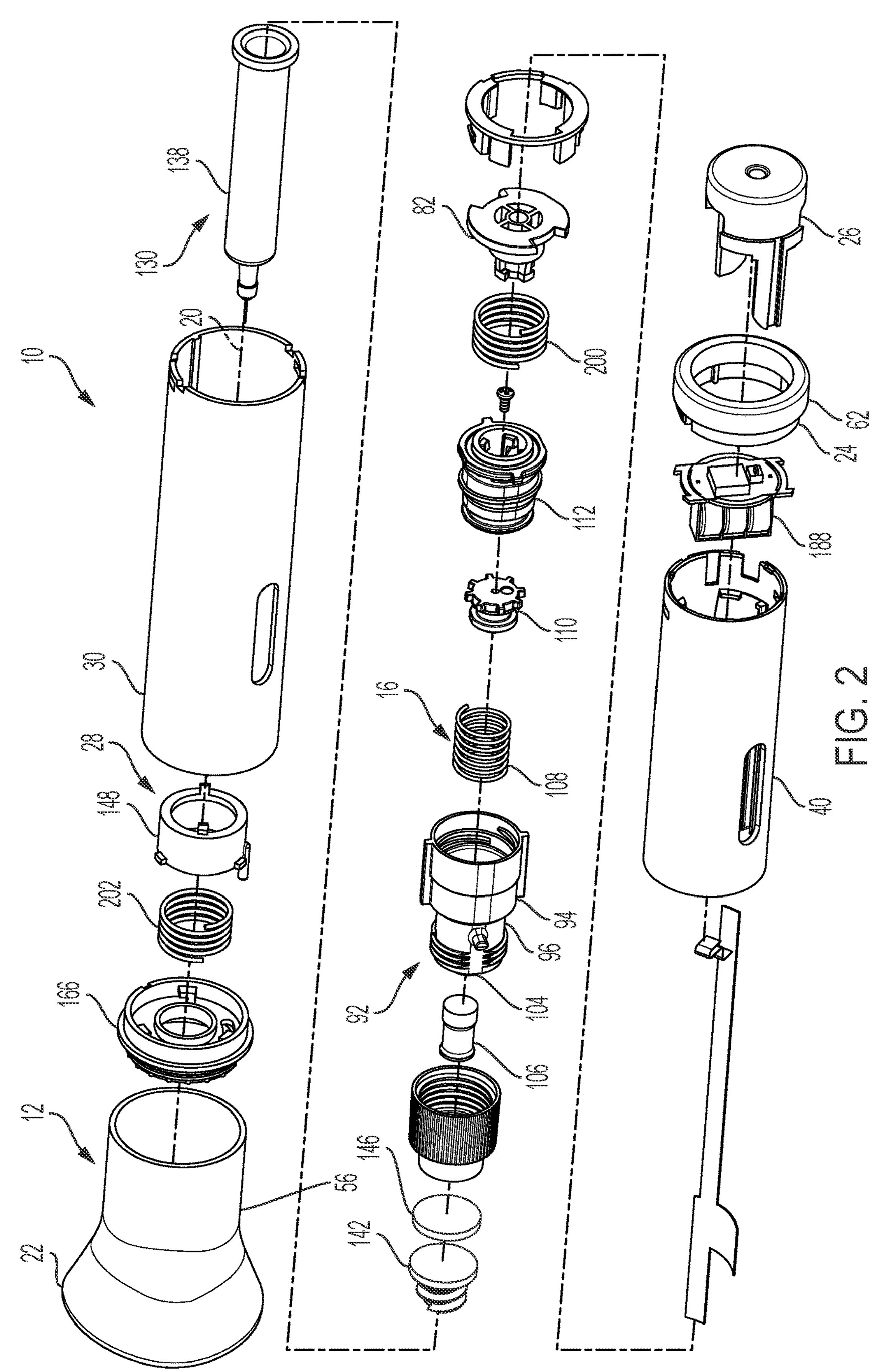
FIG. 2 is a partially exploded view of the therapeutic agent delivery system of FIG. 1.
Figure 3:
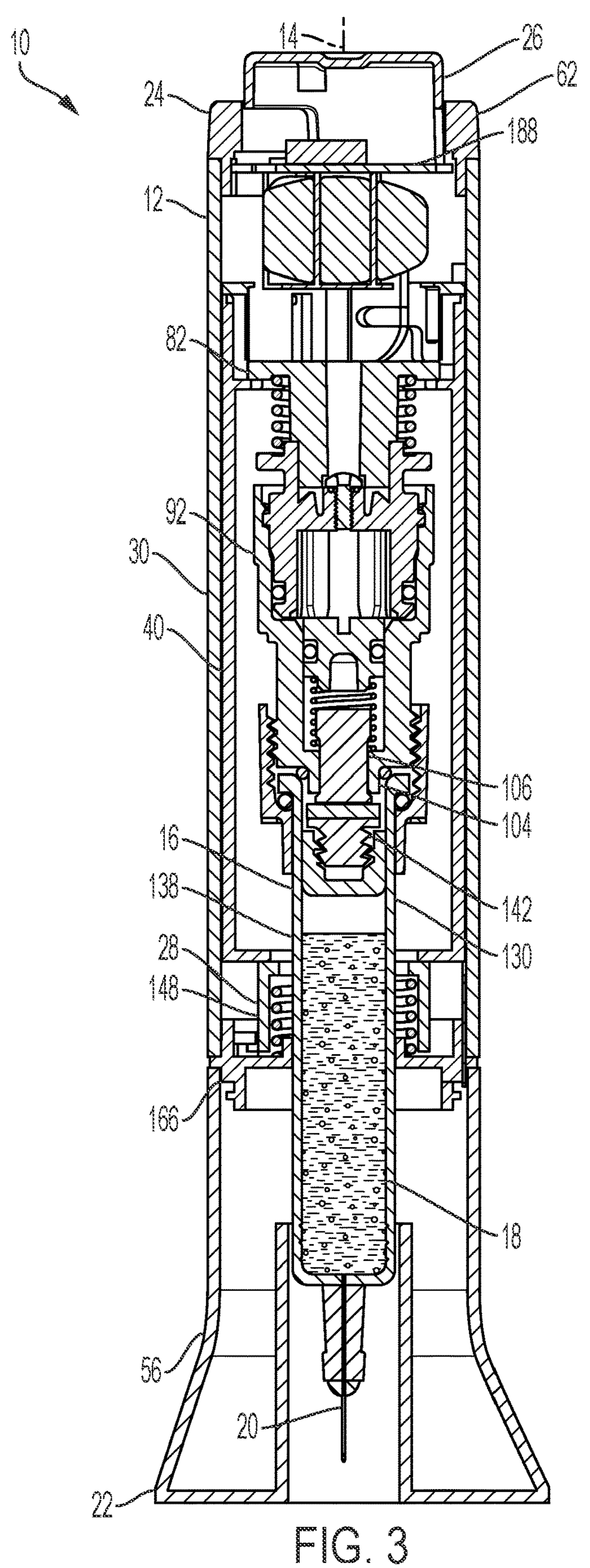
FIG. 3 is a longitudinal sectional view of the therapeutic agent delivery system of FIG. 1.

FIGS. 1-3 illustrate a therapeutic agent delivery system 10 according to an embodiment of the present disclosure. Illustratively, the therapeutic agent delivery system 10 generally includes the profile of an auto-injector pen, although other profiles may alternatively be used. Generally, the therapeutic agent delivery system 10 includes a housing 12 that is elongated along a longitudinal axis 14. The housing 12 carries a therapeutic agent delivery assembly 16. The therapeutic agent delivery assembly 16 includes a therapeutic agent 18 (see FIG. 3) and a needle 20, and the therapeutic agent delivery assembly 16 translates relative to the housing 12 from a stowed configuration (as illustratively shown in FIGS. 1-3, a configuration in which the needle 20 is disposed entirely within the housing 12) to a deployed configuration (shown elsewhere—for example, a configuration in which the needle 20 is at least partially exposed at a distal end portion 22 of the housing 12 and configured to engage the subject and deliver the therapeutic agent to the subject). A proximal end portion 24 of the therapeutic agent delivery system 10 includes a user input 26 (illustratively, a depressible button) that is actuated to actuate the therapeutic agent delivery assembly 16 (that is, move the needle 20 from the stowed configuration to the deployed configuration and deliver the therapeutic agent to the user). After actuation, the therapeutic agent delivery assembly 16 translates relative to the housing 12 from the deployed configuration to a retracted configuration (shown elsewhere—for example, a configuration in which the needle 20 is disposed entirely within the therapeutic agent delivery system 10). The therapeutic agent delivery system 10 includes a retraction mechanism 28 that translates the therapeutic agent delivery assembly 16 relative to the housing 12 from the deployed configuration to the retracted configuration. After reaching the retracted configuration, the therapeutic agent delivery assembly 16 is inhibited from being translated to the deployed configuration (stated another way, the system 10 is "locked out"). These aspects, features, and components of the therapeutic agent delivery system 10 are described in further detail below.

Figure 4:
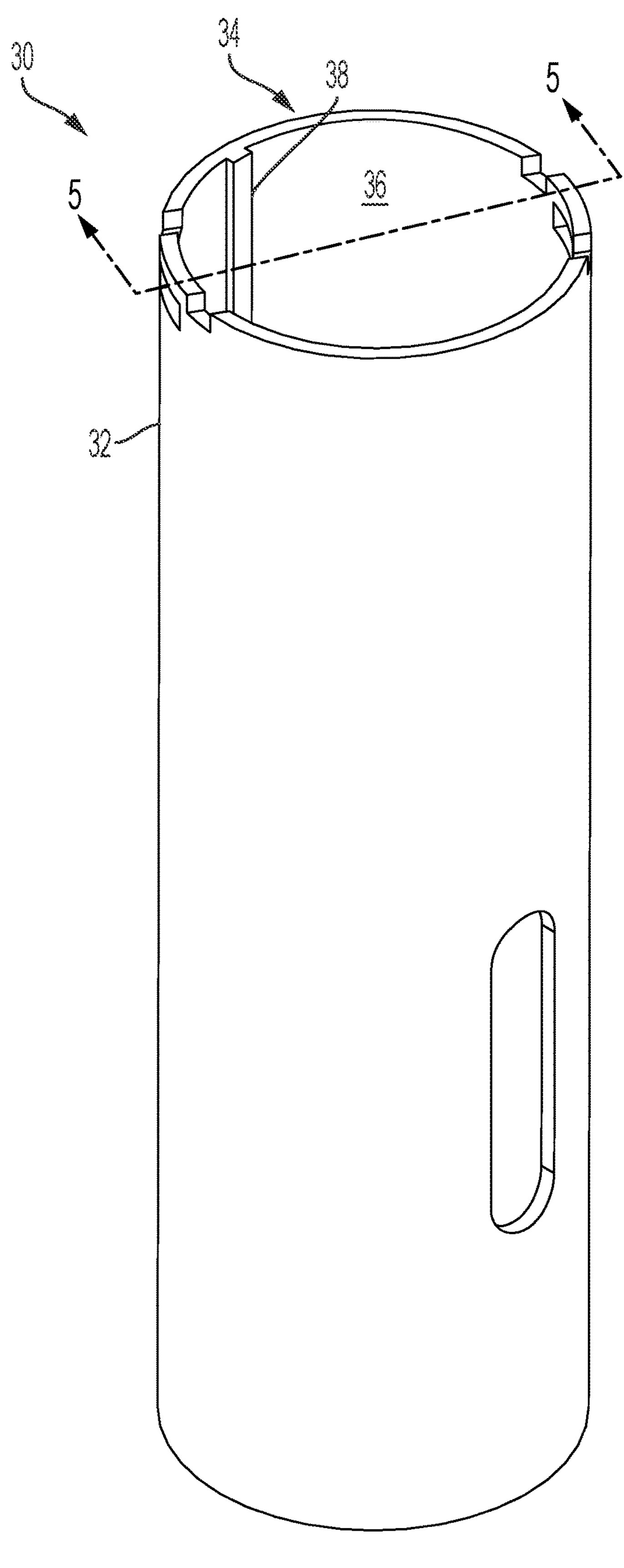
FIG. 4 is a top perspective view of a proximal outer housing portion of a housing of the therapeutic agent delivery system of FIG. 1.
Figure 5:
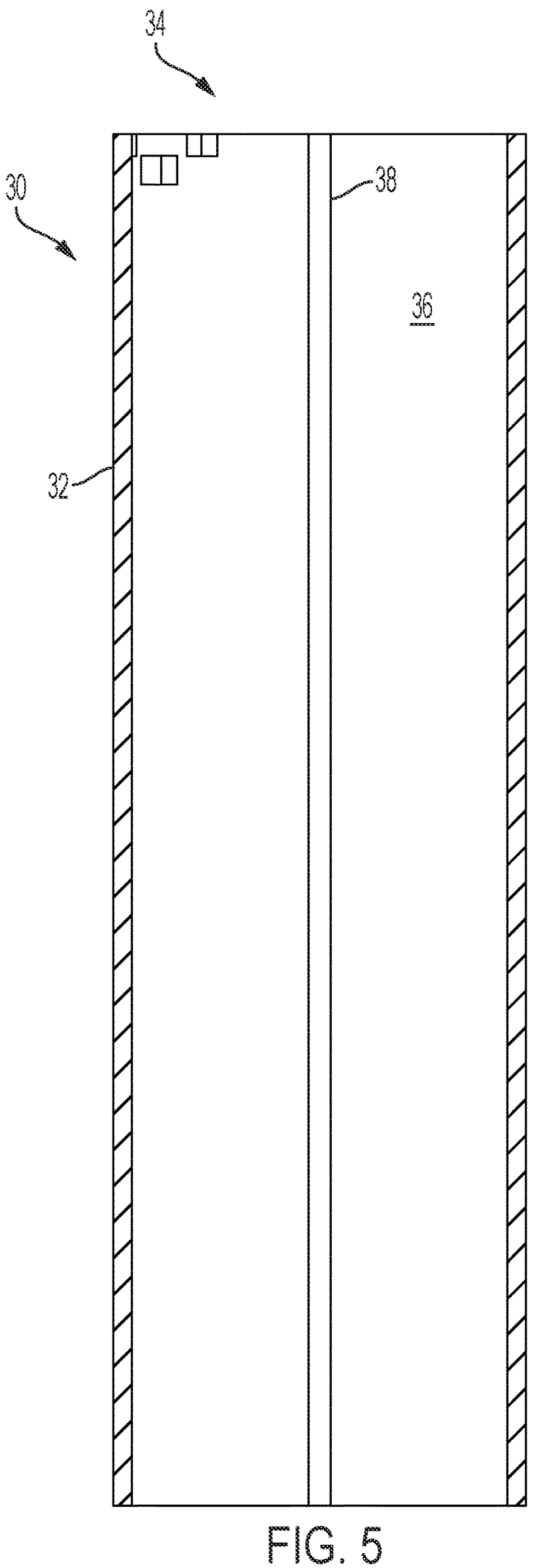
FIG. 5 is a longitudinal sectional view of the proximal outer housing portion along line 5-5 of FIG. 4.

FIGS. 4 and 5 illustrate a proximal outer housing portion 30 of the housing 12. The proximal outer housing portion 30 includes a main body 32 that has a generally cylindrical shape. The main body 32 includes an inner passageway 34 that carries other components of the therapeutic agent delivery system 10, as described in further detail below. Adjacent to the inner passageway 34, an inner surface 36 of the proximal outer housing portion 30 includes a translation feature (illustratively, an axially extending ridge 38) that facilitates translation of other components relative to the proximal outer housing portion 30.

Figure 6:
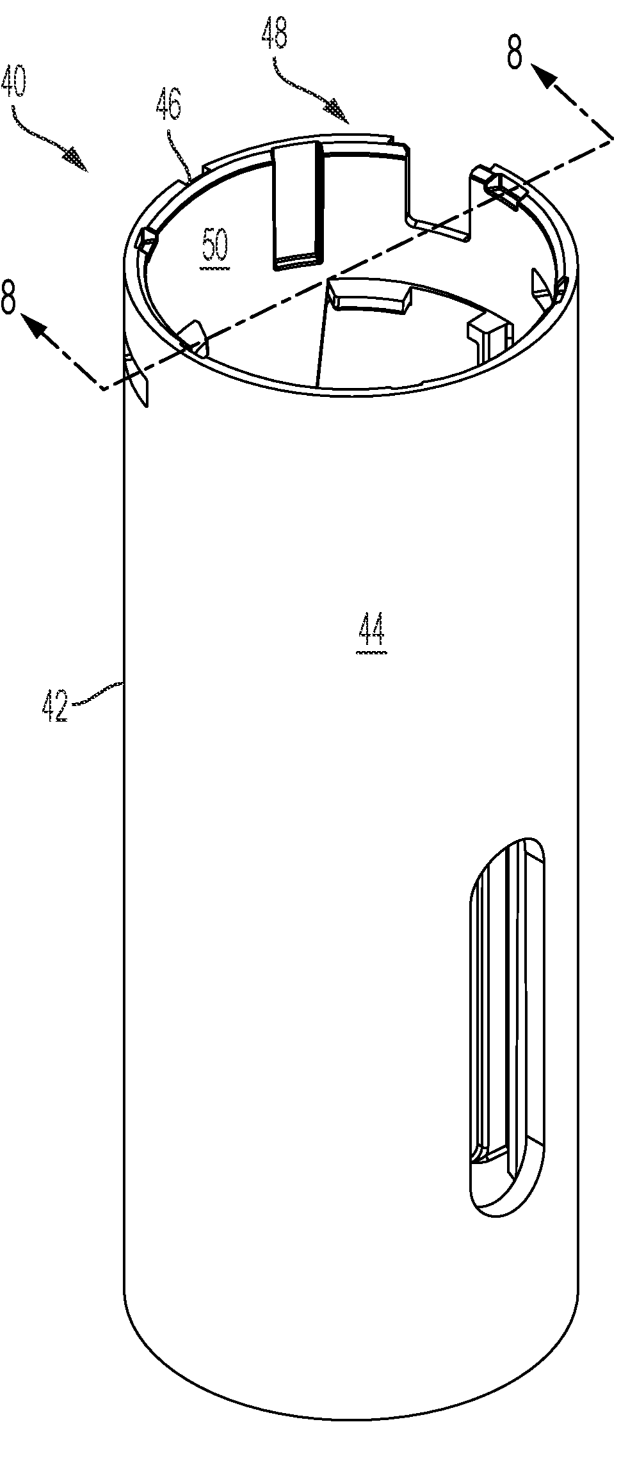
FIG. 6 is a top perspective view of a proximal inner housing portion of the housing of the therapeutic agent delivery system of FIG. 1.
Figure 7:
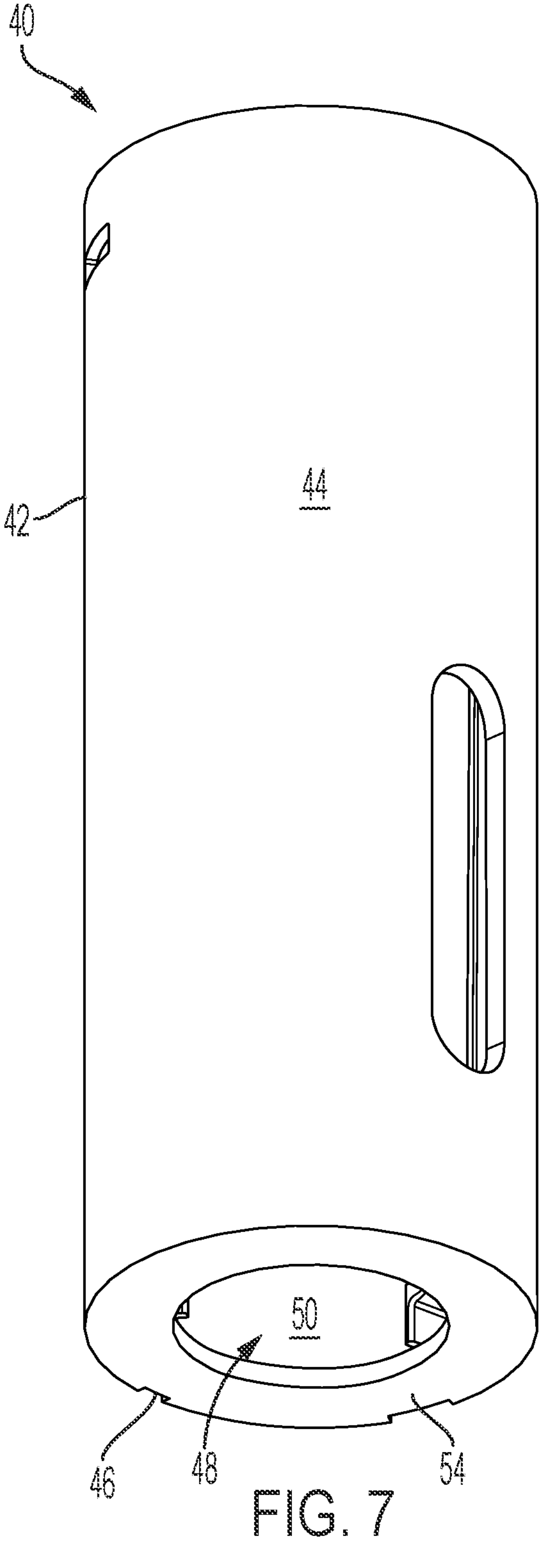
FIG. 7 is a bottom perspective view of the proximal inner housing portion of FIG. 6.
Figure 8:
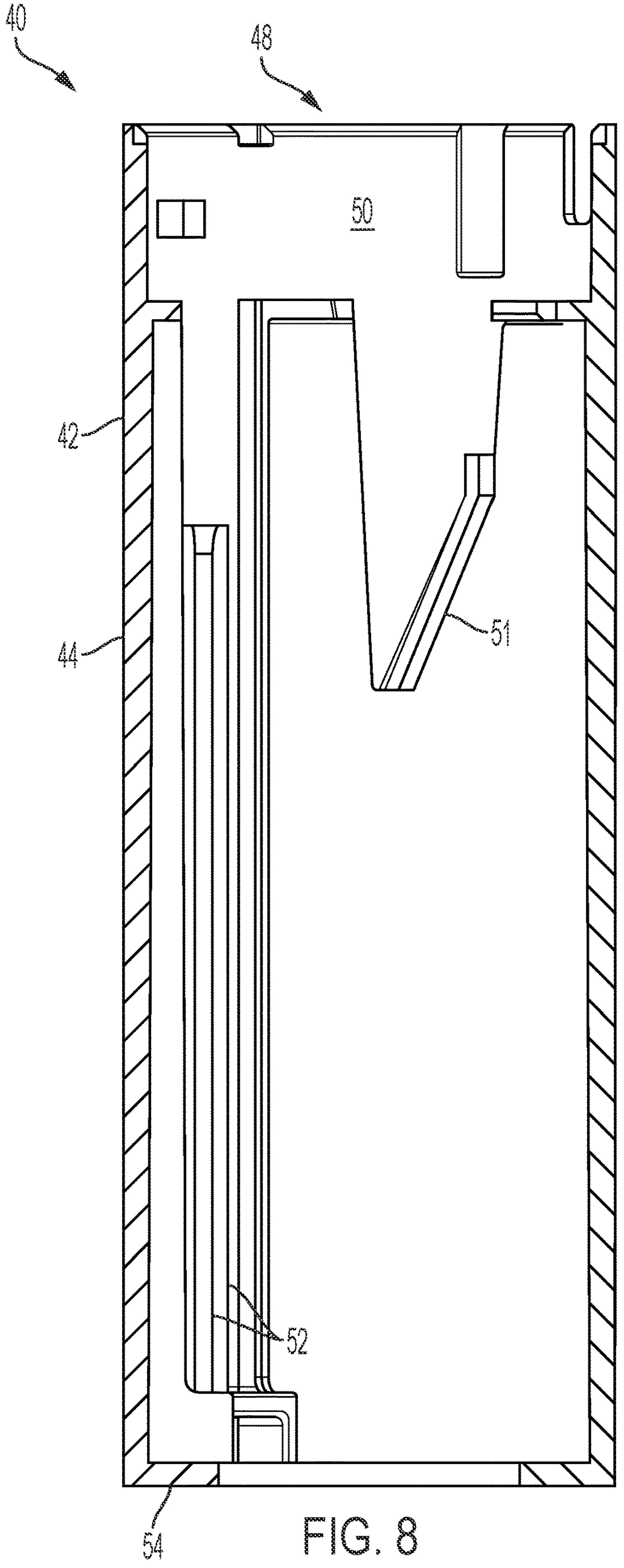
FIG. 8 is a longitudinal sectional view of the proximal inner housing portion along line 8-8 of FIG. 6.

FIGS. 6-8 illustrate a proximal inner housing portion 40 of the housing 12. The proximal inner housing portion 40 includes a main body 42 that has a generally cylindrical shape. An external surface 44 of the main body 42 includes a translation feature (illustratively, an axially extending channel 46) that couples to the translation feature of the proximal outer housing portion 30 (shown elsewhere—illustratively, the axially extending ridge 38) to facilitate translation of the proximal inner housing portion 40 relative to the proximal outer housing portion 30. The main body 42 further includes an inner passageway 48 that carries other components of the therapeutic agent delivery system 10. Adjacent to the inner passageway 48, an inner surface 50 of the proximal inner housing portion 40 includes an actuation feature (illustratively, two helically extending ramps 51, one of which is shown in FIG. 8) that, as described in further detail below, selectively engage and facilitate actuating the therapeutic agent delivery assembly 16. The inner surface 50 of the proximal inner housing portion 40 carries translation features (illustratively, two pairs of axially extending ridges 52, one pair of which is shown in FIG. 8) that facilitate translation of the therapeutic agent delivery assembly 16 relative to the proximal inner housing portion 40. The inner surface 50 also carries a biasing platform (illustratively, a radially-inwardly extending flange 54) that, as described in further detail below, carries other components and facilitates translating the therapeutic agent delivery assembly 16 from the deployed configuration to a retracted configuration.

Figure 9:
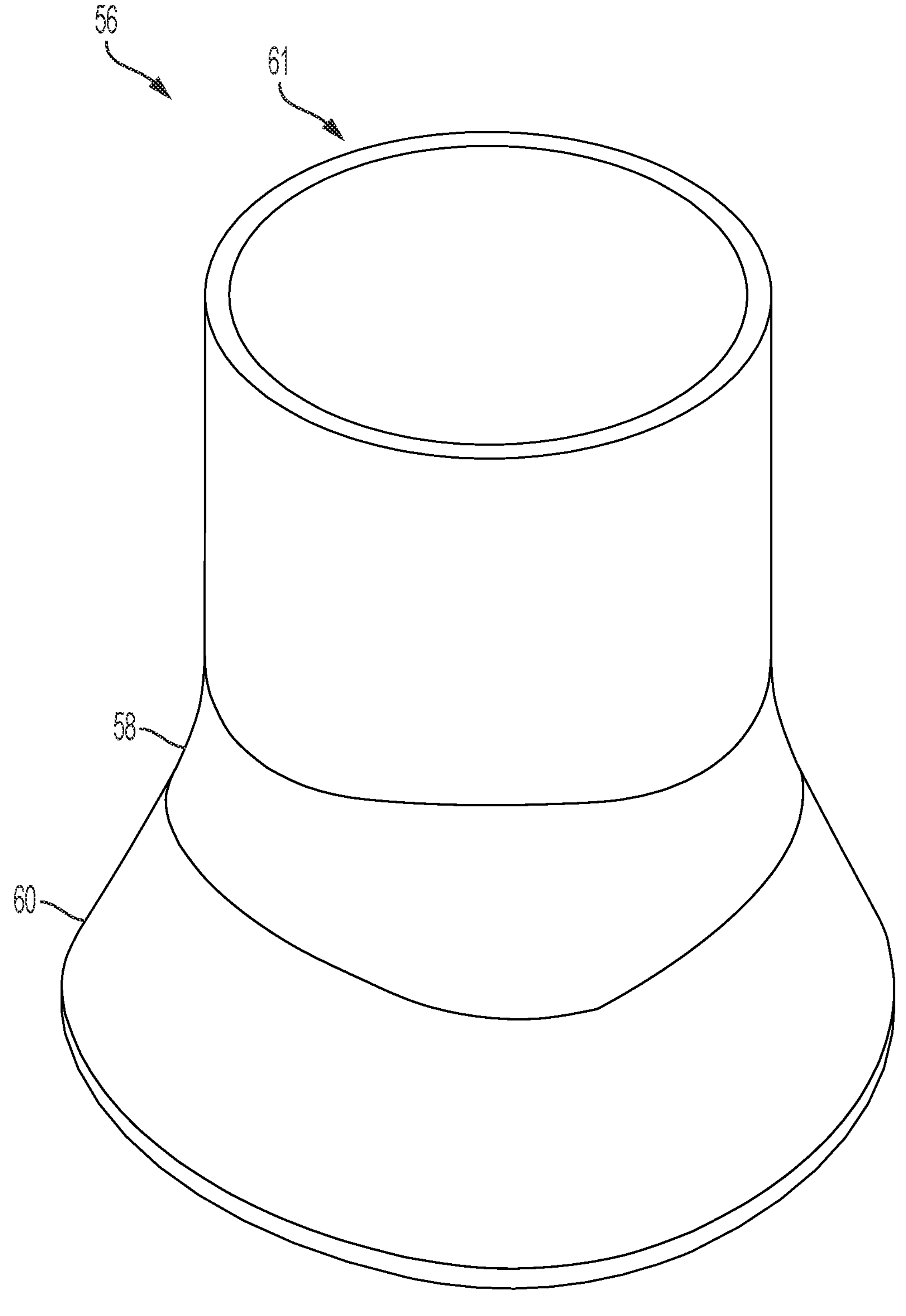
FIG. 9 is a top perspective view of a distal housing portion of the housing of the therapeutic agent delivery system of FIG. 1.
Figure 10:
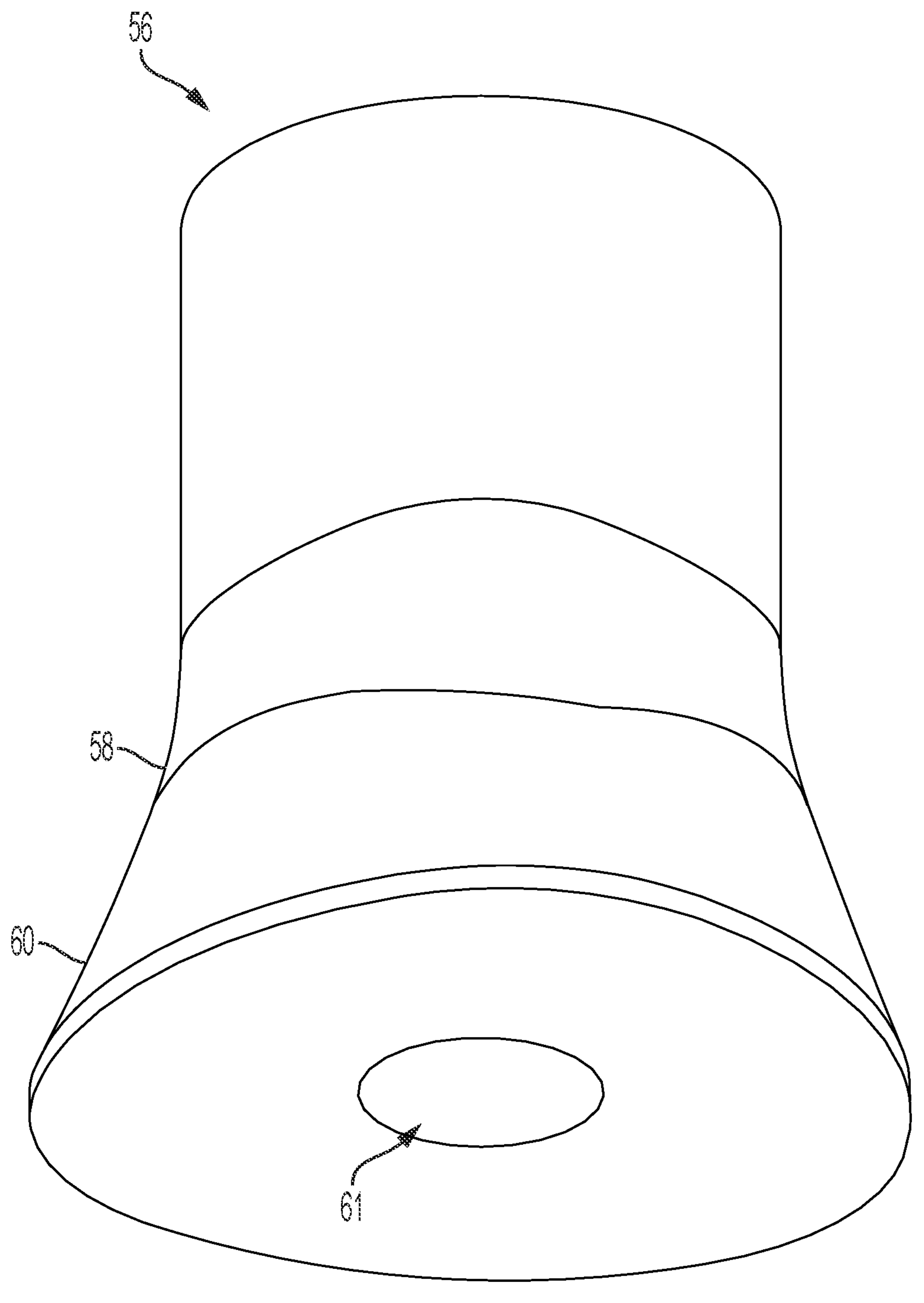
FIG. 10 is a bottom perspective view of the distal housing portion of FIG. 9.

FIGS. 9 and 10 illustrate a distal housing portion 56 of the housing 12. The distal housing portion 56 includes a main body 58 that has a generally conical shape with a flared distal end portion 60. The main body 58 includes an inner passageway 61 that carries the therapeutic agent delivery assembly 16 (shown elsewhere).

Figure 11:
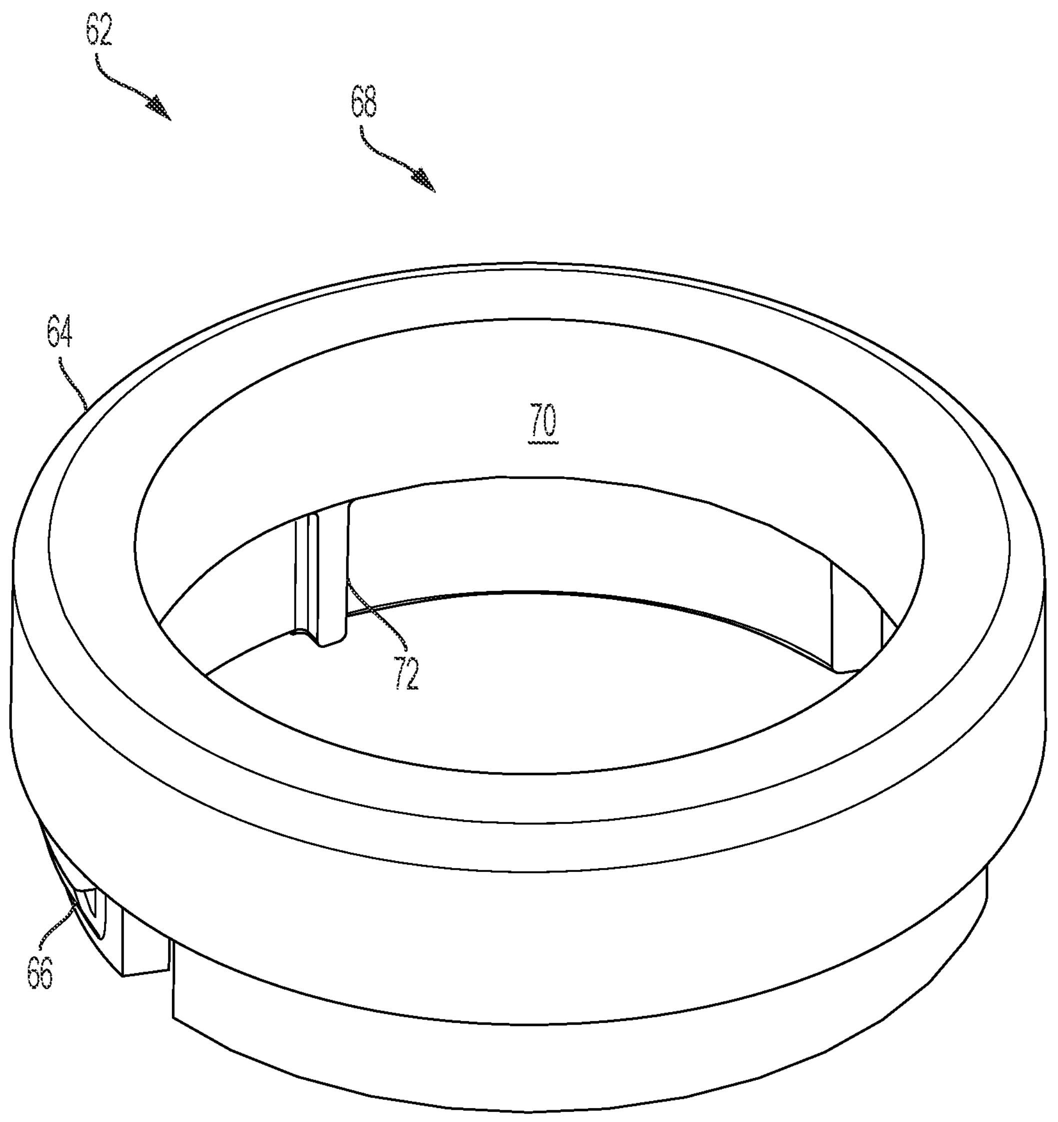
FIG. 11 is a top perspective view of a user input support of the therapeutic agent delivery system of FIG. 1.

FIG. 11 illustrates a user input support 62 of the therapeutic agent delivery system 10. The user input support 62 couples to the proximal outer housing portion 30 (shown elsewhere) at the proximal end portion 24 of the therapeutic agent delivery system 10. The user input support 62 includes a main body 64, and the main body 64 carries a coupling feature (illustratively, a plurality of snap connectors 66, one of which is shown in FIG. 11) for coupling to the proximal outer housing portion 30. The main body 64 includes an inner passageway 68 that receives the user input 26 (shown elsewhere). Adjacent to the inner passageway 68, an inner surface 70 of the user input support 62 carries a translation feature (illustratively, a plurality of axially extending ridges 72, one of which is shown in FIG. 11) that facilitates translation of the user input 26 relative to the user input support 62. In other embodiments, different arrangements of the user input support 62 are possible.

Figure 12:
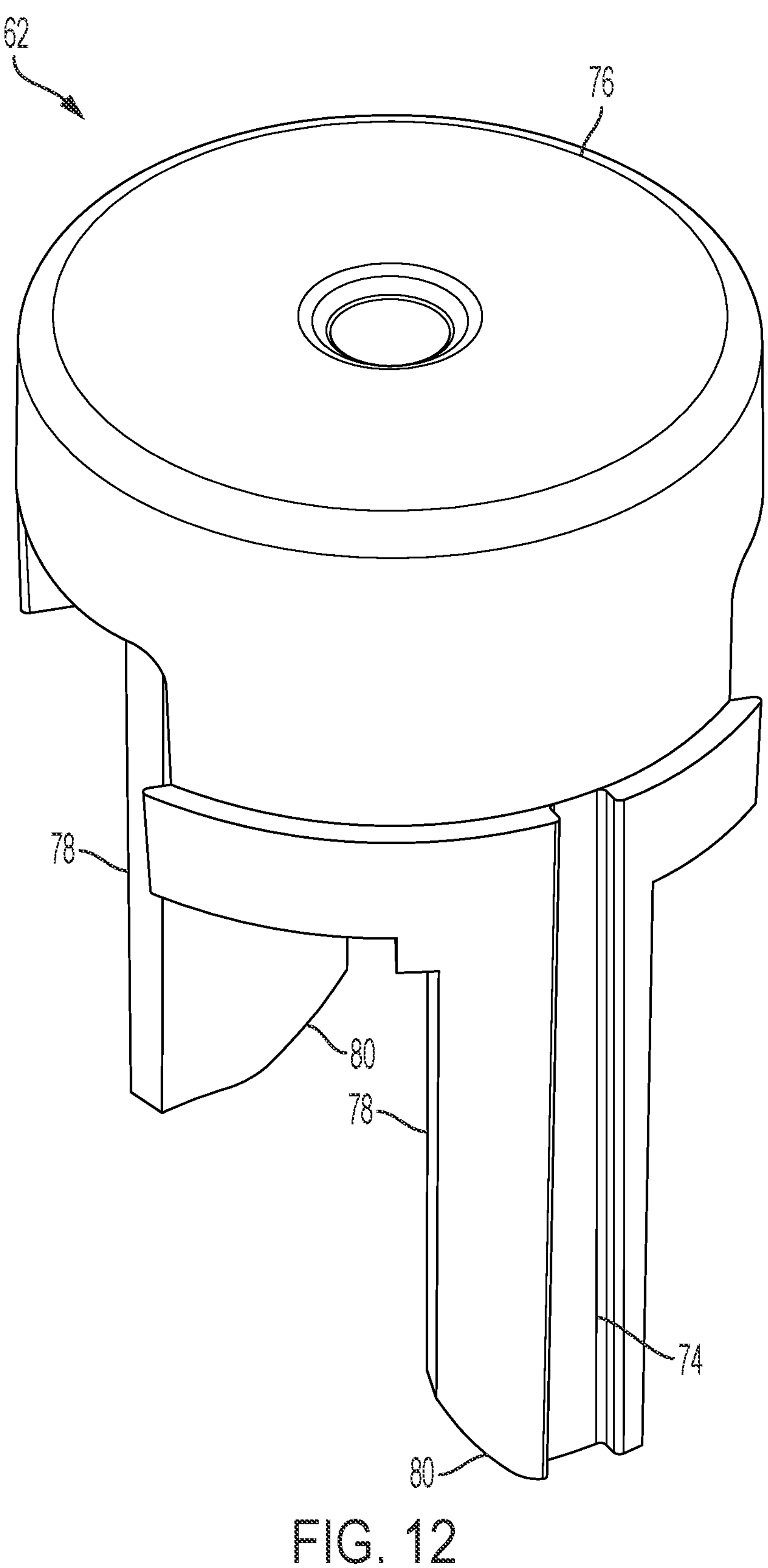
FIG. 12 is a top perspective view of a user input of the therapeutic agent delivery system of FIG. 1.

FIG. 12 illustrates the user input 26 of the therapeutic agent delivery system 10. The user input 26 includes a translation feature (illustratively, a plurality of axially extending channels 74, one of which is shown in FIG. 12) for engaging the translation feature of the user input support 62 (shown elsewhere—illustratively, the plurality of axially extending ridges 72) to facilitate translation of the user input 26 relative to the user input support 62 and the housing 12 (shown elsewhere). Adjacent to the translation feature, the user input 26 includes an exposed portion 76 that is pressed by a user to translate the user input 26 relative to the user input support 62 and the housing 12. The user input 26 also includes an actuation feature that facilitates actuating the therapeutic agent delivery assembly 16 (shown elsewhere). Illustratively, the actuation feature includes two arms 78 that are disposed opposite the exposed portion 76. Each of the arms 78 includes an actuation surface (illustratively, a helically extending surface 80). Interaction of the arms 78 with other components of the therapeutic agent delivery system 10 is described in further detail below. In other embodiments, different arrangements of the user input 26 are possible.

Figure 13:
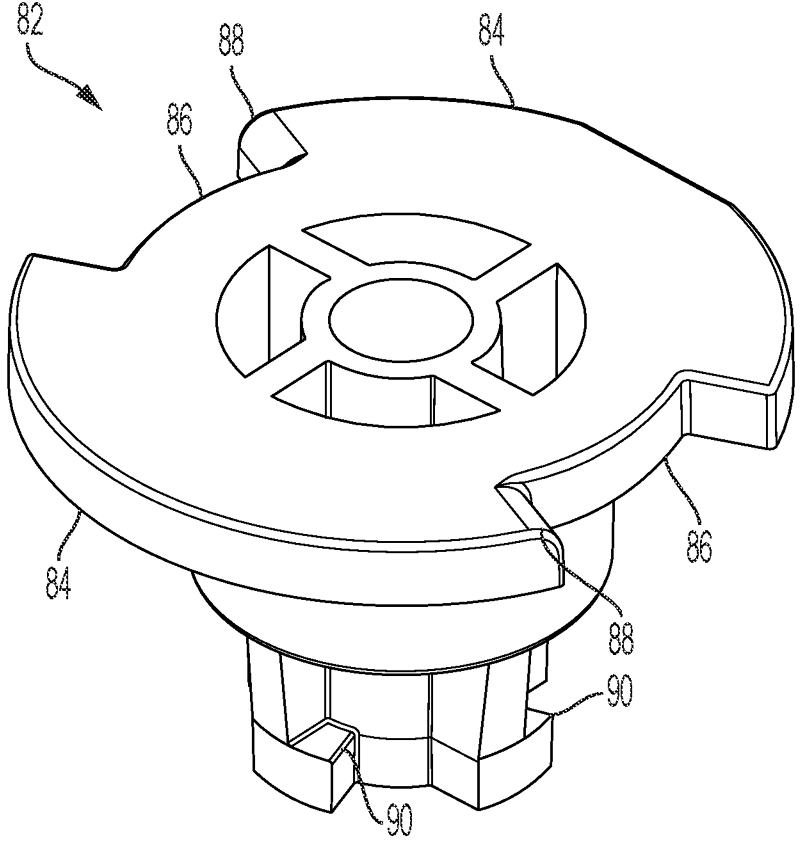
FIG. 13 is a top perspective view of an input drive of the therapeutic agent delivery system of FIG. 1.
Figure 14:
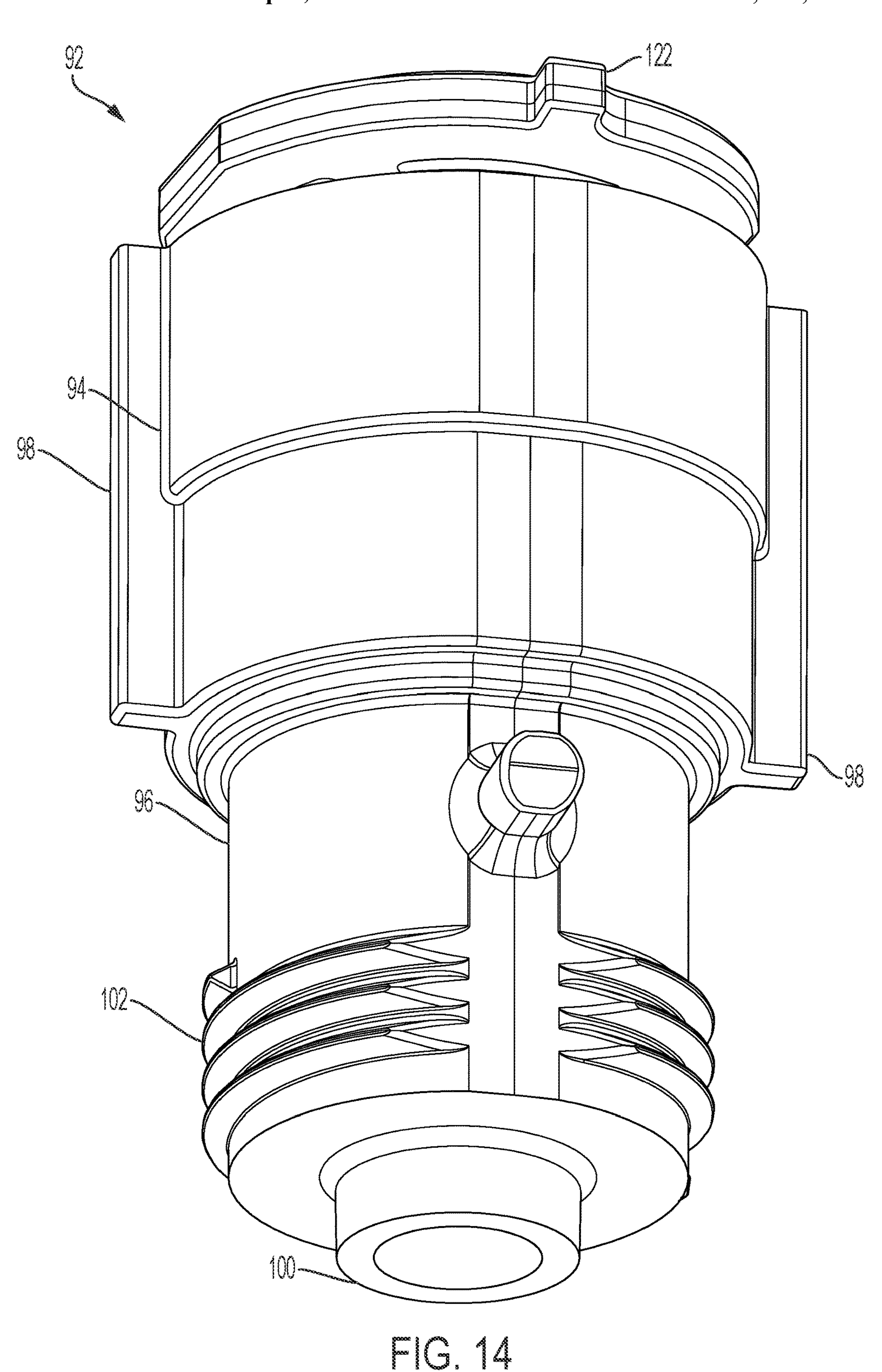
FIG. 14 is a bottom perspective view of a pressure generating actuator of a therapeutic agent delivery assembly of the therapeutic agent delivery system of FIG. 1.
Figure 15:
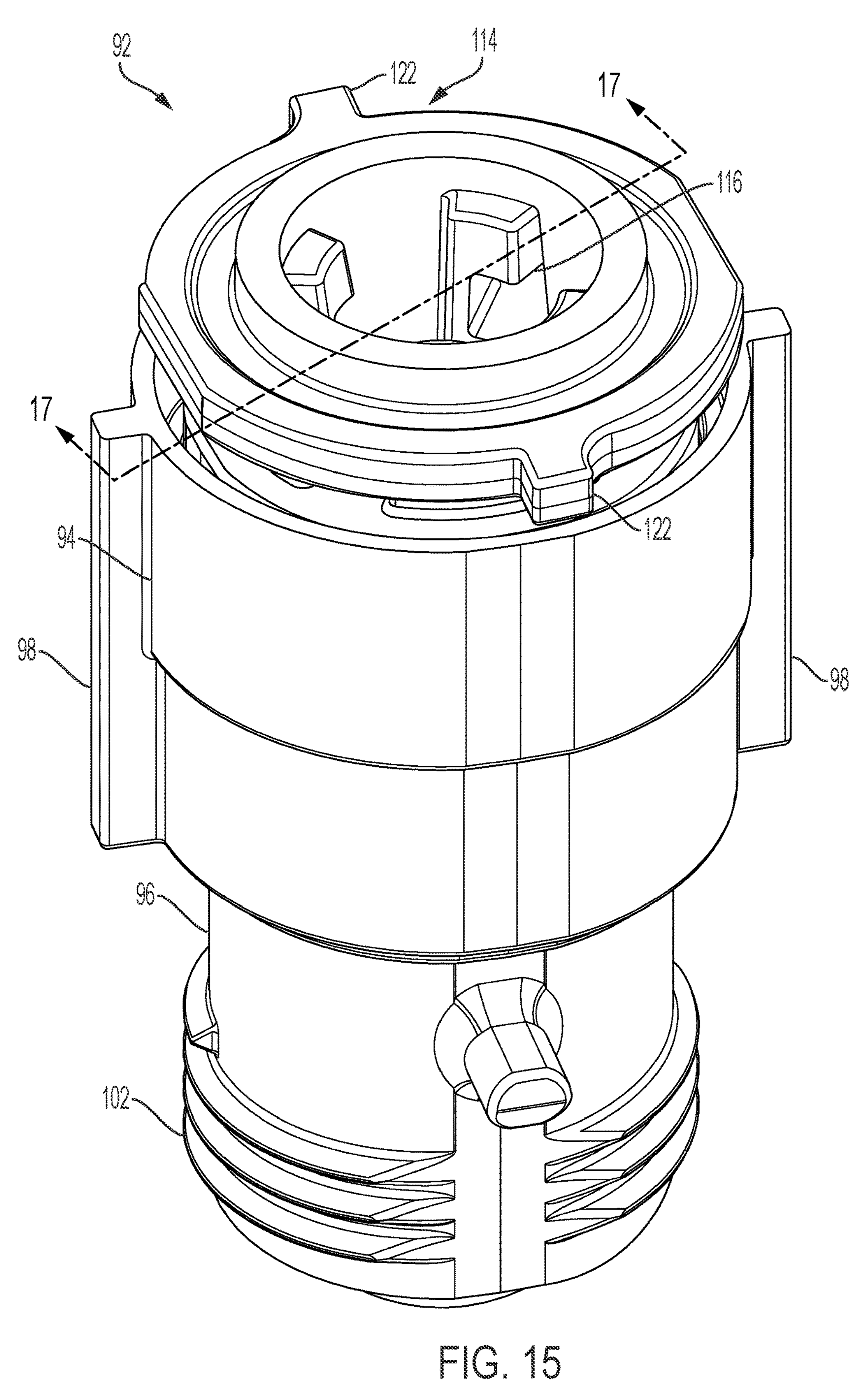
FIG. 15 is a top perspective view of the pressure generating actuator of FIG. 14.
Figure 16:
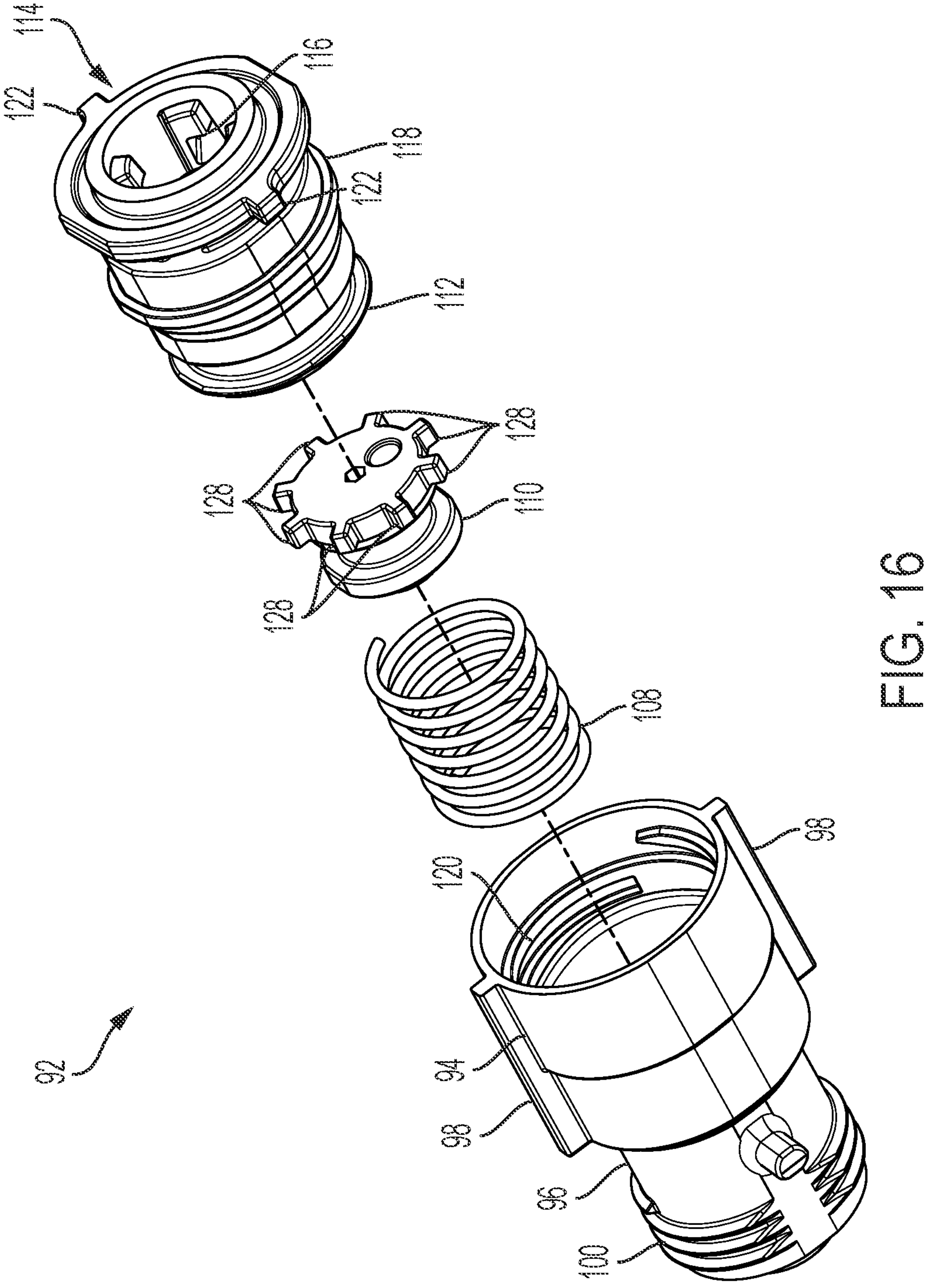
FIG. 16 is a partially exploded perspective view of the pressure generating actuator of FIG. 14.

FIG. 13 illustrates an input drive 82 of the therapeutic agent delivery system 10. The input drive 82 includes an actuation feature that is configured to interact with the actuation feature of the user input 26 (shown elsewhere). Illustratively, the actuation feature of the input drive 82 includes two partial flanges 84 and two openings 86 disposed between the partial flanges 84. Each of the partial flanges 84 includes an actuation surface (illustratively, a rounded corner 88 adjacent to one of the openings 86) that engages one of the actuation surfaces 80 of the user input 26 to facilitate rotating the input drive 82 relative to the housing 12 (shown elsewhere) upon translating the user input 26 relative to the housing 12. Opposite the actuation feature, the input drive 82 includes a detachable coupling feature (illustratively, a plurality of ledges 90 or radially-outwardly extending L-shaped protrusions 90) that detachably couples the input drive 82 to the therapeutic agent delivery assembly 16 (shown elsewhere). In other embodiments, different arrangements of the input drive 82 are possible.

FIG. 14-17 illustrate a pressure generating actuator 92 of the therapeutic agent delivery assembly 16. Generally, the pressure generating actuator 92 is actuated by the user input 26, via the input drive 82 (both shown elsewhere), to facilitate mixing of internally-carried chemical reagents, which generates one or more pressurized fluids (for example, one or more gases). Examples of suitable reagents and generated gases are provided below. As described in further detail below, the pressurized fluid(s) are delivered to and facilitate movement of other components of the therapeutic agent delivery assembly 16.

The pressure generating actuator 92 includes a first mixing chamber 94 and a second mixing chamber 96, which are illustratively monolithically formed with each other. Externally, the first mixing chamber 94 and the second mixing chamber 96 include translation features (illustratively, two axially extending ridges 98) for translatably coupling to the translation features of the proximal inner housing portion 40 (shown elsewhere—illustratively, each of the axially extending ridges 98 is translatably received by one of the pairs of axially extending ridges 52 of the proximal inner housing portion 40). As a result, the pressure generating actuator 92 is translatably carried by the proximal inner housing portion 40. At an outlet end portion 100, the mixing chambers 94, 96 include an outlet coupling feature (illustratively, an externally threaded surface 102) for coupling to another component of the therapeutic agent delivery assembly 16. The outlet end portion 100 also includes an actuator outlet 104. Pressurized fluid is discharged from the pressure generating actuator 92 via the outlet 104.

Figure 17:
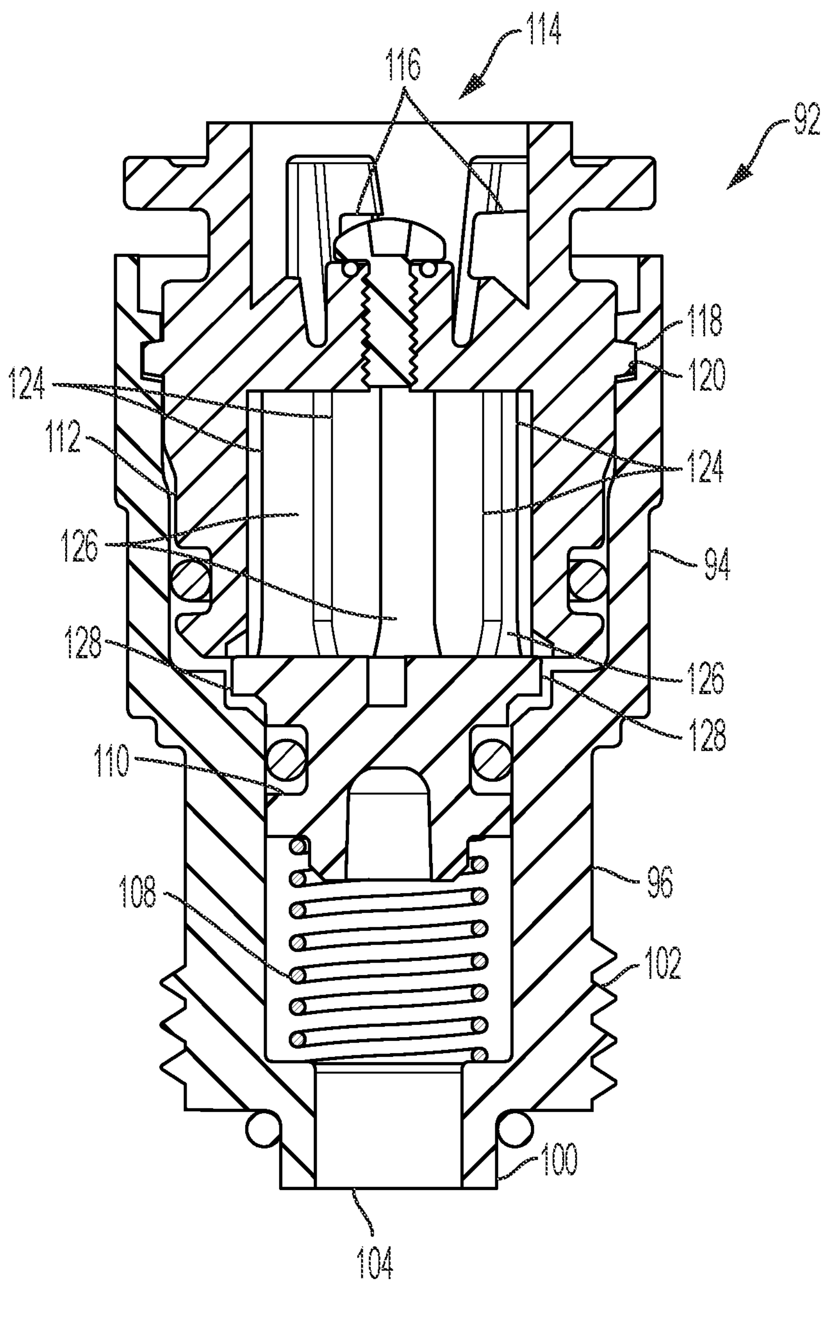
FIG. 17 is a longitudinal sectional view of the pressure generating actuator along line 17-17 of FIG. 15.
Figure 19:
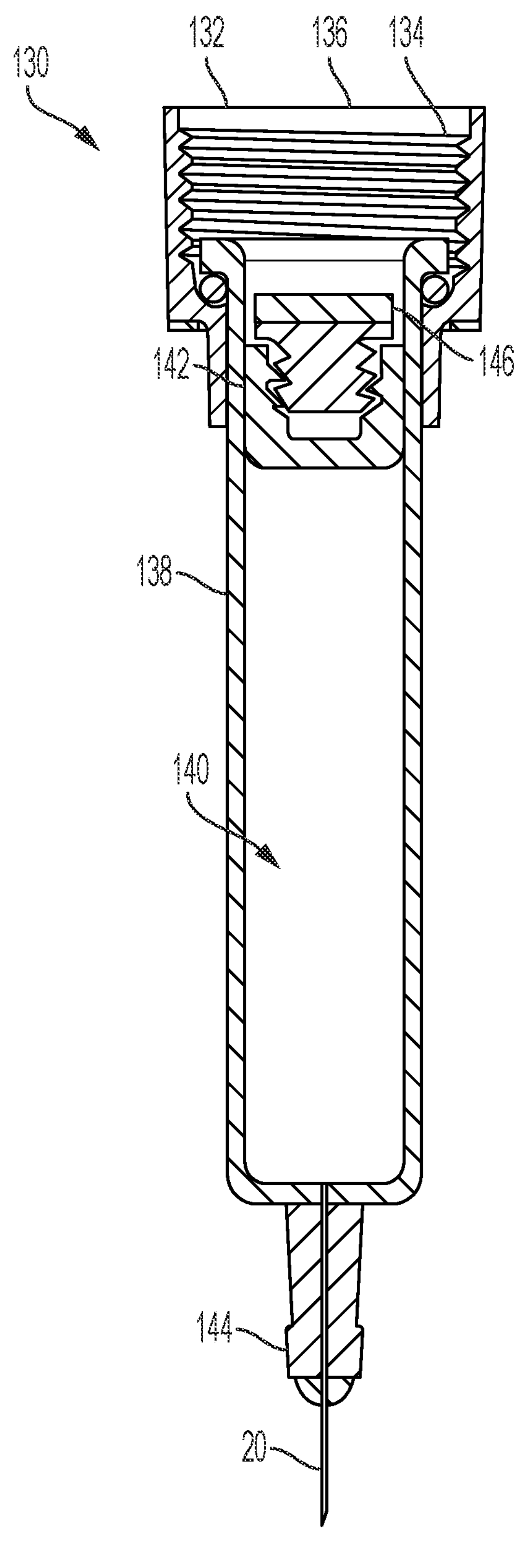
FIG. 19 is a longitudinal sectional view of the syringe assembly along line 19-19 of FIG. 18.

Internally, the mixing chambers 94, 96 carry an actuator spring 108, a mixing piston 110, and a rotatable shuttle 112 in an axially stacked arrangement. The rotatable shuttle 112 includes a recess 114, and the recess 114 carries a detachable coupling feature (illustratively, a plurality of ledges 116 or radially-outwardly extending L-shaped protrusions 116) that engages the detachable coupling feature of the input drive 82 (illustratively, the plurality of ledges 90). The first mixing chamber 94 and the shuttle 112 form a helical coupling for movably coupling to each other. Illustratively, the shuttle 112 includes a helically extending ridge 118 and the first mixing chamber 94 includes a helically extending groove 120 that receives the ridge 118. The shuttle 112 includes an actuation feature (illustratively, two radially-outwardly extending fingers 122) that, as described in further detail below, engage and are driven by the actuation feature of the proximal inner housing portion 40 (shown elsewhere—illustratively, the two helically extending ramps 51). Internally, the shuttle 112 includes a first restraining feature (illustratively, eight radially-inwardly extending tabs 124, four of which are shown in FIG. 17) that engages the mixing piston 110. Illustratively, the shuttle 112 also includes channels 126 (three of which are shown in FIG. 17) disposed between adjacent tabs 124. The mixing piston 110 includes a second restraining feature (illustratively, eight radially-outwardly extending tabs 128) that engages the first restraining feature of the shuttle 112. Initially and as shown in FIG. 19, the first restraining feature engages the second restraining feature (illustratively, the radially-inwardly extending tabs 124 of the shuttle 112 are angularly aligned with and engage the radially-outwardly extending tabs 128 of the mixing piston 110) to hold the mixing piston 110 in a position between the first mixing chamber 94 and the second mixing chamber 96. The mixing piston 110 thereby maintains separation of reagents in the first mixing chamber 94 and the second mixing chamber 96. Initially the actuator spring 108 is also compressed within the second mixing chamber 96 against the mixing piston 110. In a subsequent configuration, as described in further detail below, the shuttle 112 rotates relative to the first mixing chamber 94 and the second mixing chamber 96 to disengage the first restraining feature from the second restraining feature (illustratively, the radially-inwardly extending tabs 124 of the shuttle 112 are angularly misaligned with, or angularly offset from, the radially-outwardly extending tabs 128 of the mixing piston 110, and the channels 126 are angularly aligned with the radially-outwardly extending tabs 128 of the mixing piston 110). As a result, the actuator spring 108 expands and moves the mixing piston 110 into the shuttle 112 and the first mixing chamber 94, which permits the reagents in the first mixing chamber 94 and the second mixing chamber 96 to mix. Mixing of the reagents generates one or more pressurized fluids (for example, one or more gases), and the pressurized fluid(s) are delivered to other components of the therapeutic agent delivery assembly 16.

In some embodiments, pressure generating actuators 92 have different structures. For example, suitable pressure generating actuators 92 include those described in: U.S. Pat. No. 9,795,740 titled "Chemical Engines and Methods for Their Use, Especially in the Injection of Highly Viscous Fluids"; U.S. Publication No. 2020/0030537, titled "Processes and Devices for Delivery of Fluid by Chemical Reaction"; and International Publication No. WO2019/050791, titled "System for Controlling Gas Generation with a Drug Delivery Device", the disclosures of which are expressly incorporated herein by reference in their entireties.

Any suitable chemical reagent or reagents can be used to generate one or more pressurized fluids in pressure generating actuators 92 of the present disclosure. Examples of generated gases include carbon dioxide gas, nitrogen gas, oxygen gas, chlorine gas, etc. Desirably, the generated gas is inert and non-flammable. The amount of gas needed to facilitate movement of other components of the therapeutic agent delivery assembly 16 may impact the type, amount, and concentration of each reagent used in pressure generating actuators 92. The reagents may be in dry form (for example, powdered form, tablet form) and/or in liquid form.

In one exemplary embodiment, a bicarbonate (which may be present in dry form) reacts with an acid (which may be present in liquid form) to produce carbon dioxide gas in pressure generating actuators 92. Examples of suitable bicarbonates include sodium bicarbonate, potassium bicarbonate, and ammonium bicarbonate. Other ingredients may also be present along with the bicarbonates, such as diatomaceous earth. Examples of suitable acids include acetic acid, citric acid, potassium bitartrate, disodium pyrophosphate, and calcium dihydrogen phosphate. In one particular example, the bicarbonate is potassium bicarbonate and the acid is aqueous citric acid, which may react to produce carbon dioxide gas and a liquid mixture of water and dissolved potassium citrate.

In some embodiments, other reactions may be used. In one example, a metal carbonate, such as copper carbonate or calcium carbonate, is thermally decomposed to produce carbon dioxide gas and the corresponding metal oxide in pressure generating actuators 92. In another example, 2,2'-azobisisobutyronitrile (AIBN) is heated to produce nitrogen gas in pressure generating actuators 92. In yet another example, enzymes (for example yeast) are reacted with sugar to produce carbon dioxide gas in pressure generating actuators 92. Some substances readily sublime, going from solid to gas. Such substances include but are not limited to naphthalene and iodine. In still yet another example, hydrogen peroxide is decomposed with catalysts such as enzymes (for example catalase) or manganese dioxide to produce oxygen gas in pressure generating actuators 92. In still yet another example, silver chloride is decomposed through exposure to light to generate a gas in pressure generating actuators 92. Suitable reagents, chemical formulations, and reactions are further described in the above-incorporated U.S. Pat. No. 9,795,740, U.S. Publication No. 2020/0030537, and International Publication No. WO2019/050791.

As described briefly above and referring briefly again to FIGS. 2 and 3, the outlet 104 of the pressure generating actuator 92 may carry one or more absorbent materials 106. Such absorbent materials 106 may absorb excess liquid provided by mixing the reagents within the pressure generating actuator 92. Suitable absorbent materials are further described in the above-incorporated U.S. Publication No. 2020/0030537.

Figure 18:
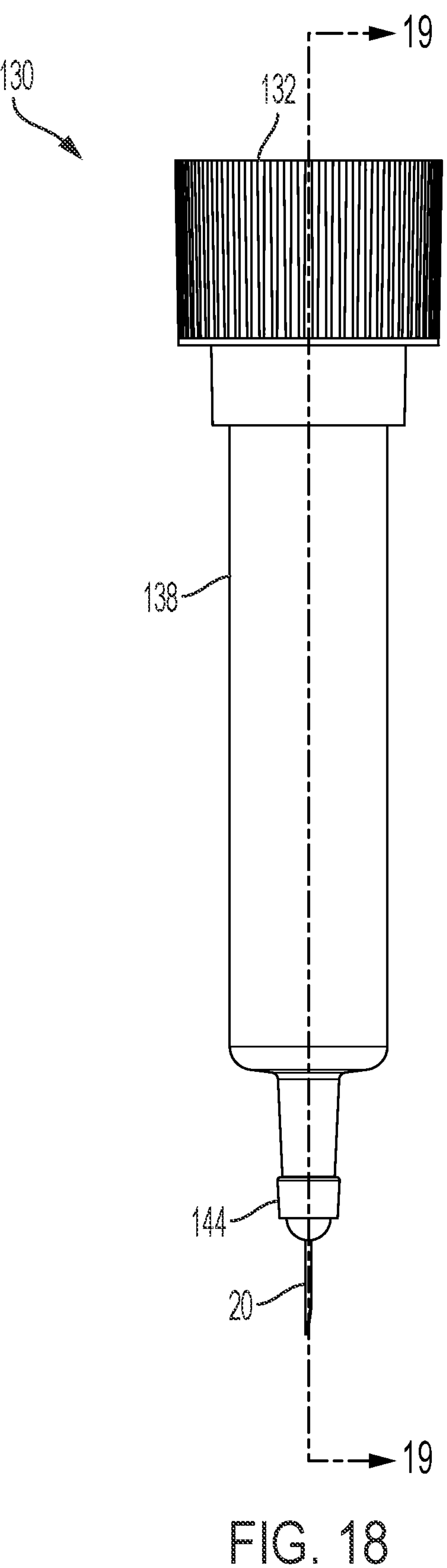
FIG. 18 is a side view of a syringe assembly of the therapeutic agent delivery assembly of the therapeutic agent delivery system of FIG. 1.

FIGS. 18 and 19 illustrate a syringe assembly 130 of the therapeutic agent delivery assembly 16. The syringe assembly 130 includes an inlet portion 132, and the inlet portion 132 includes an inlet coupling feature (illustratively, an internally threaded surface 134) that couples to the outlet coupling feature of the pressure generating actuator 92 (shown elsewhere—illustratively, the externally threaded surface 112). The inlet portion 132 also includes an inlet 136 that receives pressurized fluid(s) from the outlet 104 of the pressure generating actuator 92. The inlet portion 132 couples to a syringe chamber 138, and the syringe chamber 138 includes a syringe passageway 140 that receives the pressurized fluid(s) from the inlet portion 132. The syringe passageway 140 carries a syringe piston 142, and the syringe piston 142 translates away from the inlet portion 132 and towards an outlet portion 144 of the syringe assembly 130 when the syringe passageway 140 receives the pressurized fluid(s). Illustratively and as described in further detail below, the syringe piston 142 carries a magnetic component 146, which may also be referred to as a target, that facilitates determining the position of the syringe piston 142 in the syringe passageway 140. The syringe passageway 140 also carries the therapeutic agent 18 (shown elsewhere—illustratively, 2.25 mL of the therapeutic agent, although other volumes, including, for example, 0.5 mL, 1.0 mL, 3.0 mL or 5 mL may alternatively be carried) between the syringe piston 142 and the outlet portion 144, more specifically the needle 20. As such, translation of the syringe piston 142 in the syringe passageway 140 causes the needle 20 to discharge the therapeutic agent therefrom. In other embodiments, different arrangements are possible. For example, the inlet portion 132 and the syringe chamber 138 may be monolithically formed with each other, or the syringe assembly 130 could be replaced by another type of therapeutic agent container, such as a bellows or bladder structure.

Figure 20:
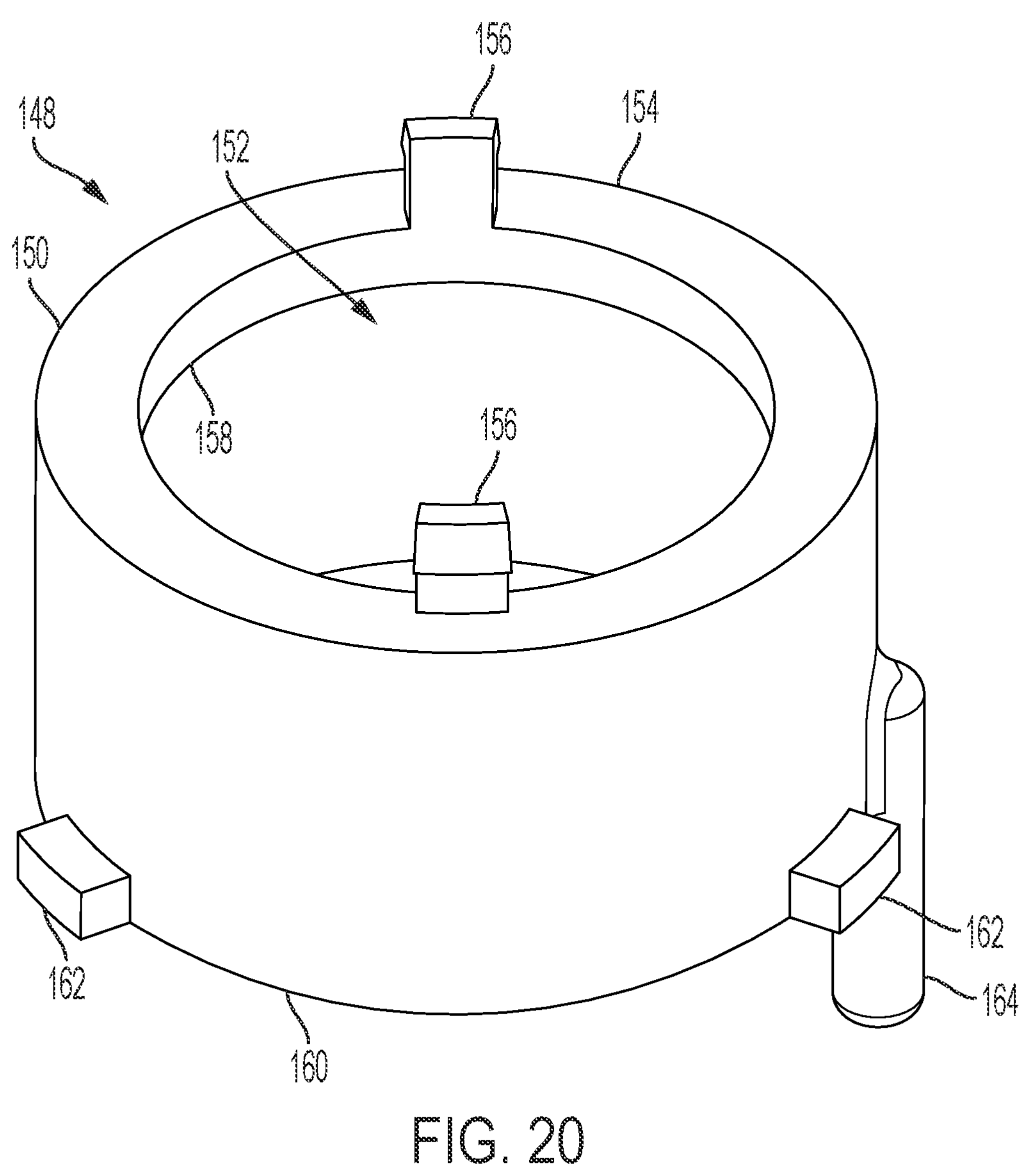
FIG. 20 is a top perspective view of a retraction cap of a retraction mechanism of the therapeutic agent delivery system of FIG. 1.

FIG. 20 illustrates a retraction cap 148 of the retraction mechanism 28 (shown elsewhere). Illustratively, the retraction cap 148 includes a main body 150 that has a generally cylindrical shape, and the main body 150 includes an inner passageway 152. A proximal end portion 154 of the main body 150 carries a coupling feature (illustratively, a plurality of snap connectors 156) for coupling the retraction cap 148 to the proximal inner housing portion 40 (shown elsewhere). The proximal end portion 154 of the main body 150 further carries a biasing platform (illustratively, a radially-inwardly extending flange 158) that, as described in further detail below, engages a spring (shown elsewhere) to facilitate reconfiguring the system 10 from the deployed configuration to the retracted configuration. A distal end portion 160 of the main body 150 carries a detachable coupling feature (illustratively, a plurality of ledges 162 or radially-outwardly extending protrusions 162, two of which are shown in FIG. 20) that detachably couples the retraction cap 148 to another component of the retraction mechanism 28, as described in further detail below. The distal end portion 160 of the main body 150 further carries a retraction feature (illustratively, an axially extending post 164) that, as described in further detail below, engages another component of the retraction mechanism 28 to facilitate reconfiguring the system 10 from the deployed configuration to the retracted configuration.

Figure 21:
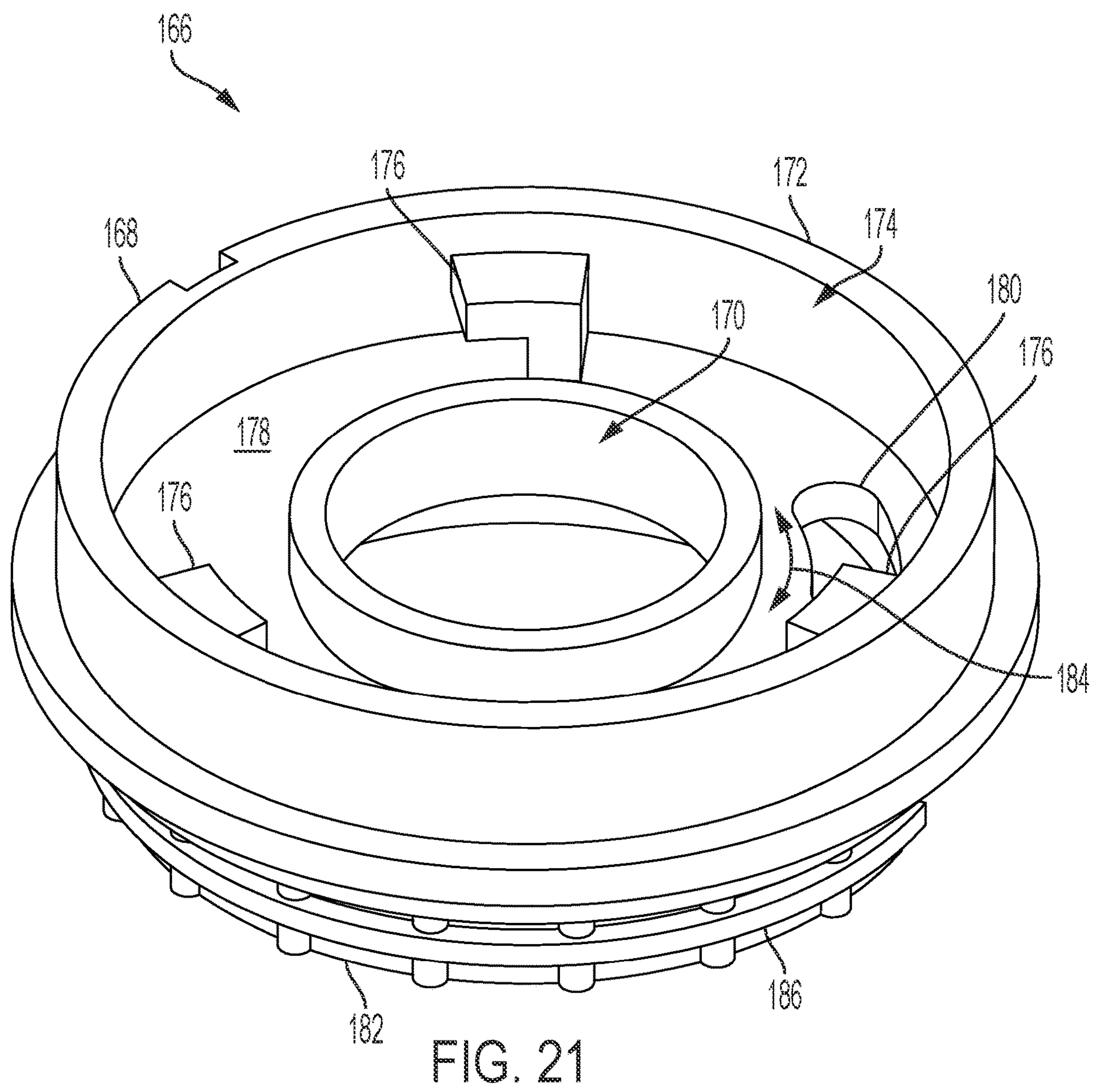
FIG. 21 is a top perspective view of a retraction base of the retraction mechanism of the therapeutic agent delivery system of FIG. 1.
Figure 22:
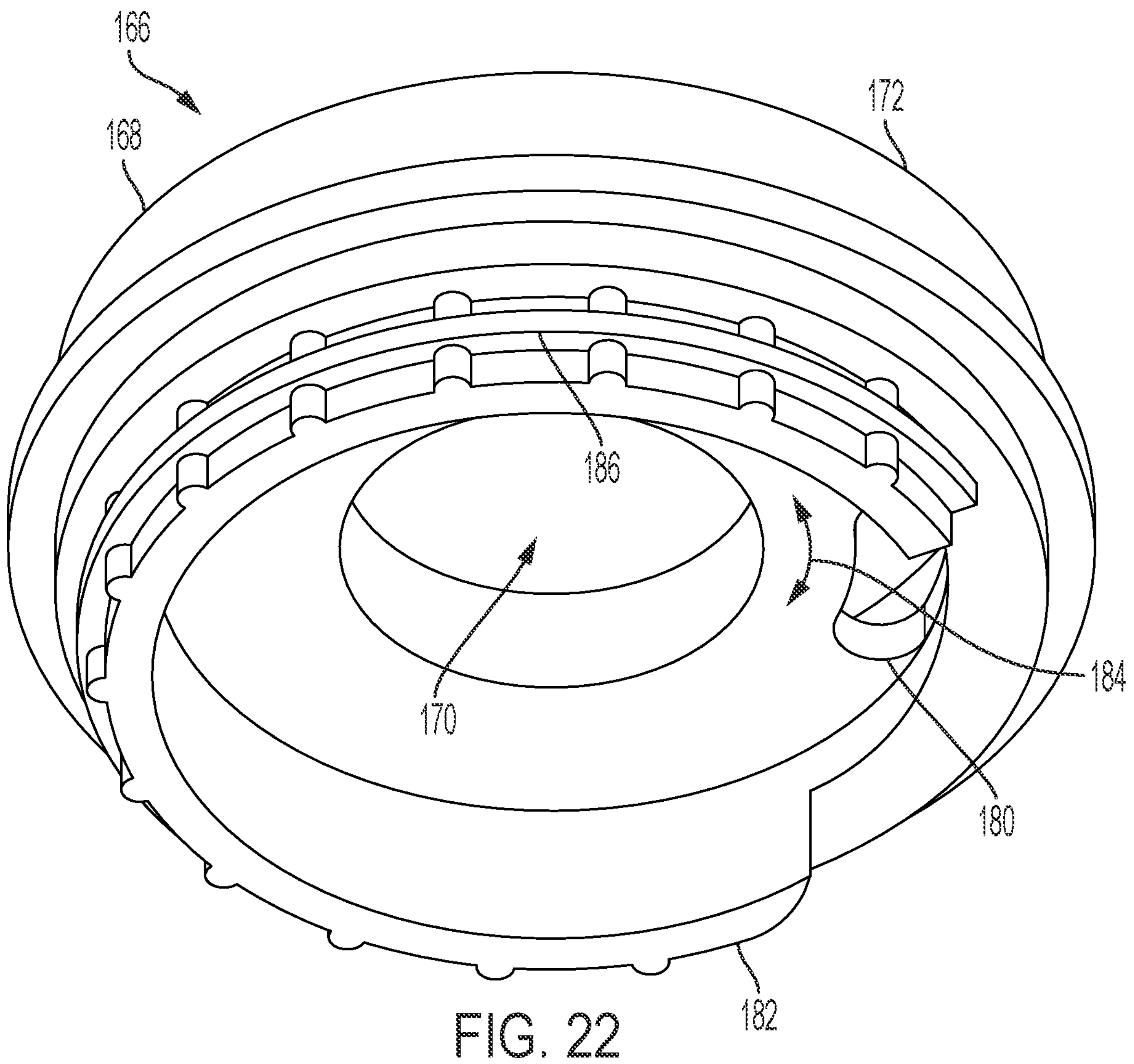
FIG. 22 a bottom perspective view of the retraction base of FIG. 21.

FIGS. 21 and 22 illustrate a retraction base 166 of the retraction mechanism 28 (shown elsewhere). Illustratively, the retraction base 166 includes a main body 168 that has a generally annular shape, and the main body 168 includes an inner passageway 170. A proximal end portion 172 of the main body 168 includes a recess 174, and the recess 174 carries a detachable coupling feature (illustratively, a plurality of ledges 176 or radially-inwardly extending L-shaped protrusions 176) that engages the detachable coupling feature of the retraction cap 148 (shown elsewhere—illustratively, the plurality of ledges 162). The recess 174 further includes a biasing platform (illustratively, a proximally-facing surface 178) that, as described in further detail below, engages the same spring (shown elsewhere) as the retraction cap 148. The recess 174 further includes an opening 180 that extends from the proximal end portion 172 to an opposite distal end portion 182. The opening 180 is elongated in a circumferential or angular direction 184. As described in further detail below, the opening 180 receives the retraction feature of the retraction cap 148 (shown elsewhere—illustratively, the axially extending post 164). Illustratively, the post 164 extends through the opening 180, and the post 164 is movable in the opening 180 in the angular direction 184. The distal end portion 182 of the main body 168 further includes a mounting surface (illustratively, a radially-outwardly facing surface 186) that, as described in further detail below, carries another component of the retraction mechanism 28.

Figure 23:
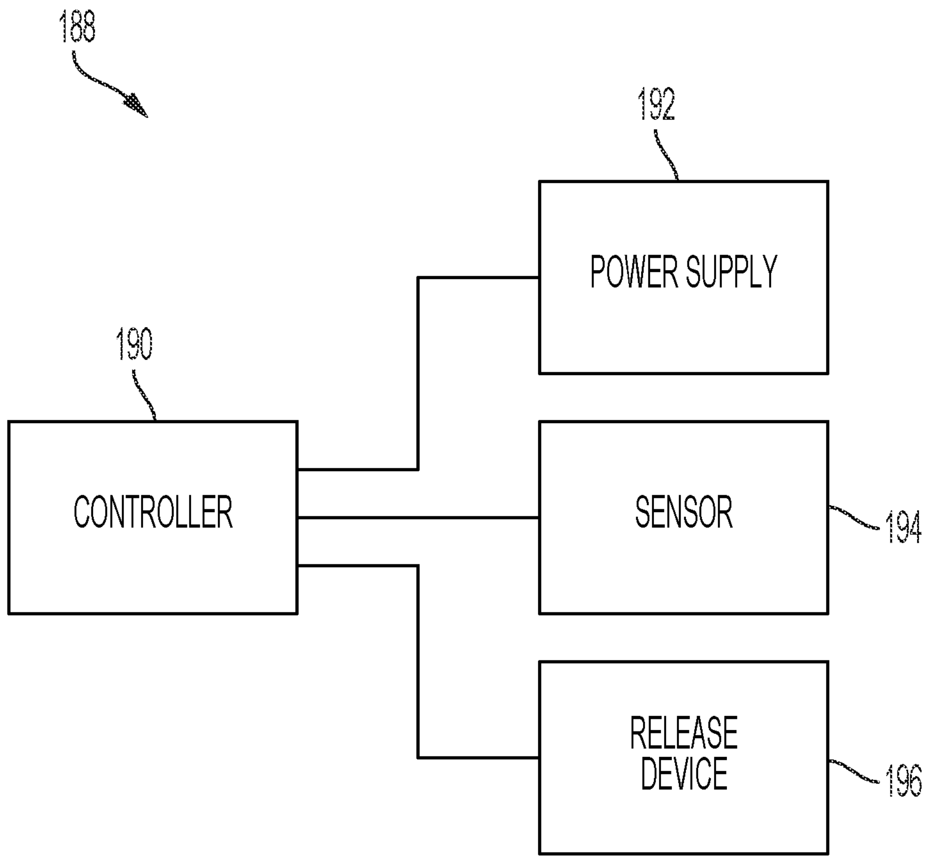
FIG. 23 is a schematic representation of an electronics assembly of the therapeutic agent delivery system of FIG. 1.
Figure 24:
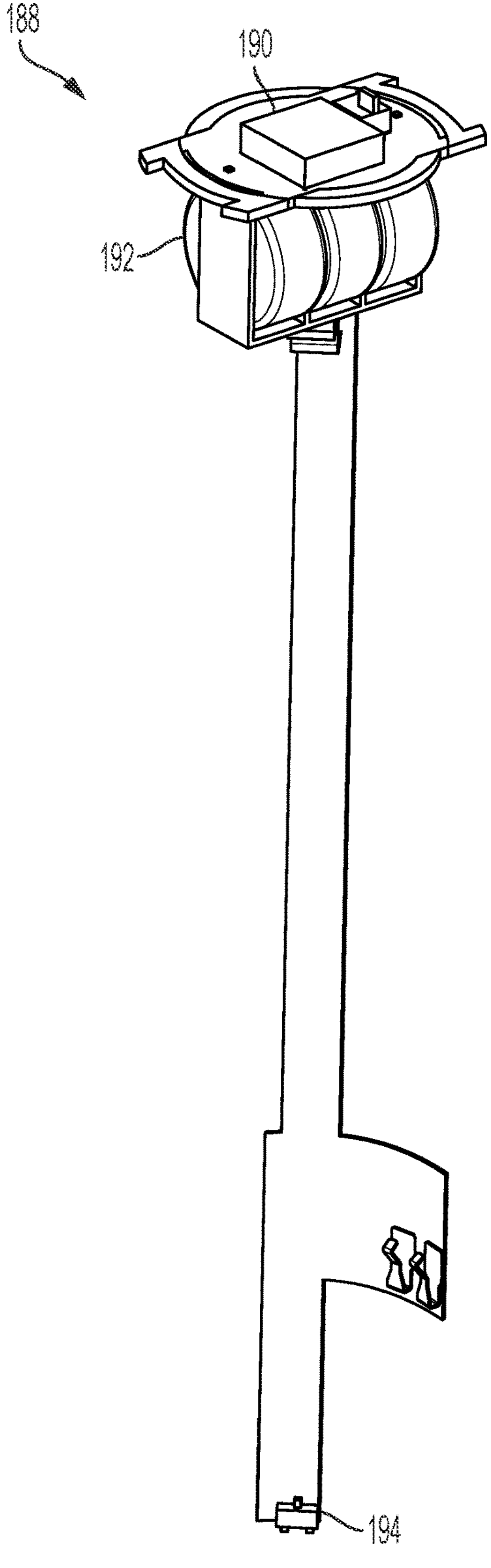
FIG. 24 is a top perspective view of the electronics assembly of FIG. 23.

FIGS. 23 and 24 illustrate an electronics assembly 188 of the therapeutic agent delivery system 10. The electronics assembly 188 includes an electronic controller 190 that is operatively coupled to and receives power from a power supply 192 (illustratively, a battery). The controller 190 is also operatively coupled to a sensor 194. The sensor 194 may send a sensor signal to the controller 190 in response to sensing various types of inputs. For example, the sensor 194 may be configured to determine the position of the syringe piston 142 in the syringe chamber 138 (both shown elsewhere—for example, to determine if the syringe piston 142 has been moved toward the syringe outlet portion 144, thereby indicating that the therapeutic agent has been discharged from the needle 20). More specifically, the sensor 194 may be a hall effect sensor that is configured to sense the magnetic component 146 (shown elsewhere) carried by the syringe piston 142. As another example, the sensor 194 may be an optical sensor or a vibration sensor. As yet another example, the sensor 194 and/or target 146 may be configured to sense and send the sensor signal to the controller 190 upon actuation of the user input 26 (shown elsewhere).

With specific reference to FIGS. 23, the controller 190 is also operatively coupled to a release device 196 of the retraction mechanism 28 (shown elsewhere). The controller 190 may send a retraction signal to the release device 196 (for example, upon receiving the sensor signal, or after a predetermined time period if the sensor 194 senses when the user input 26 is actuated) to actuate the release device 196. The retraction mechanism 28 may thereby reconfigure the system 10 from the deployed configuration to the retracted configuration. Further details of the release device 196 are described below.

Figure 25:
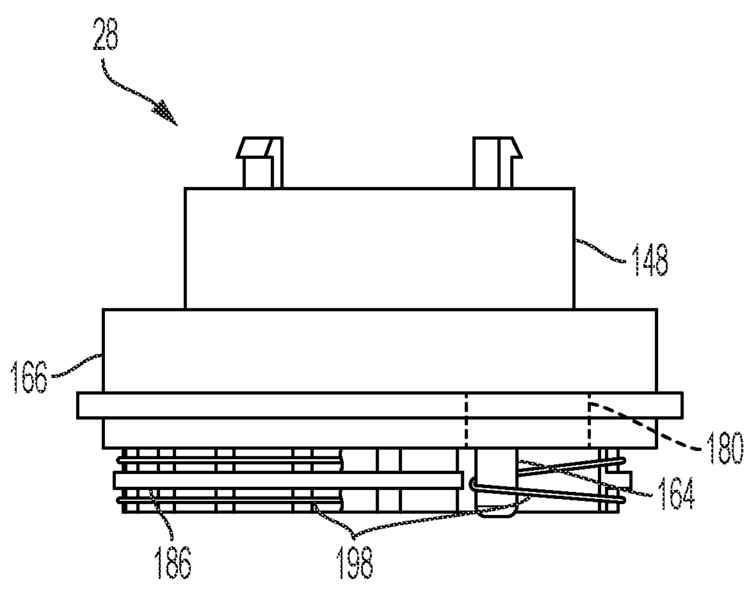
FIG. 25 is a side view of the retraction mechanism of the therapeutic agent delivery system of FIG. 1.

FIG. 25 illustrates the retraction mechanism 28, including a wire 198 that illustratively forms the release device 196. The wire 198 that extends about the outwardly facing surface 186 of the retraction base 166 and loops around the post 164 of the retraction cap 148. The wire 198 may contract or otherwise pull the post 164 such that the post 164 slides in the opening 180 of the retraction base 166. The retraction cap 148 thereby rotates relative to the retraction base 166, which disengages the detachable coupling features of the retraction cap 148 and the retraction base 166 (shown elsewhere—illustratively, the ledges 162 and 172). As described in further detail below, this action permits a spring (shown elsewhere) carried between the retraction cap 148 and the retraction base 166 to expand and urge the retraction cap 148 and the retraction base 166 apart. This action in turn reconfigures the system 10 from the deployed configuration to the retracted configuration.

Illustratively, the wire 198 may comprise one or more shape memory materials that contract upon receiving thermal energy. For example, the wire 198 may comprise a shape memory alloy, such as nitinol, and the controller 190 may provide the retraction signal to the wire 198 as an electric current to thereby heat and contract the wire 198. Alternatively, these components could take other forms. For example, the controller 190 could provide the retraction signal to a separate heating element (not shown), and the heating element could provide thermal energy to the wire 198 to thereby contract the wire 198.

Figure 26:
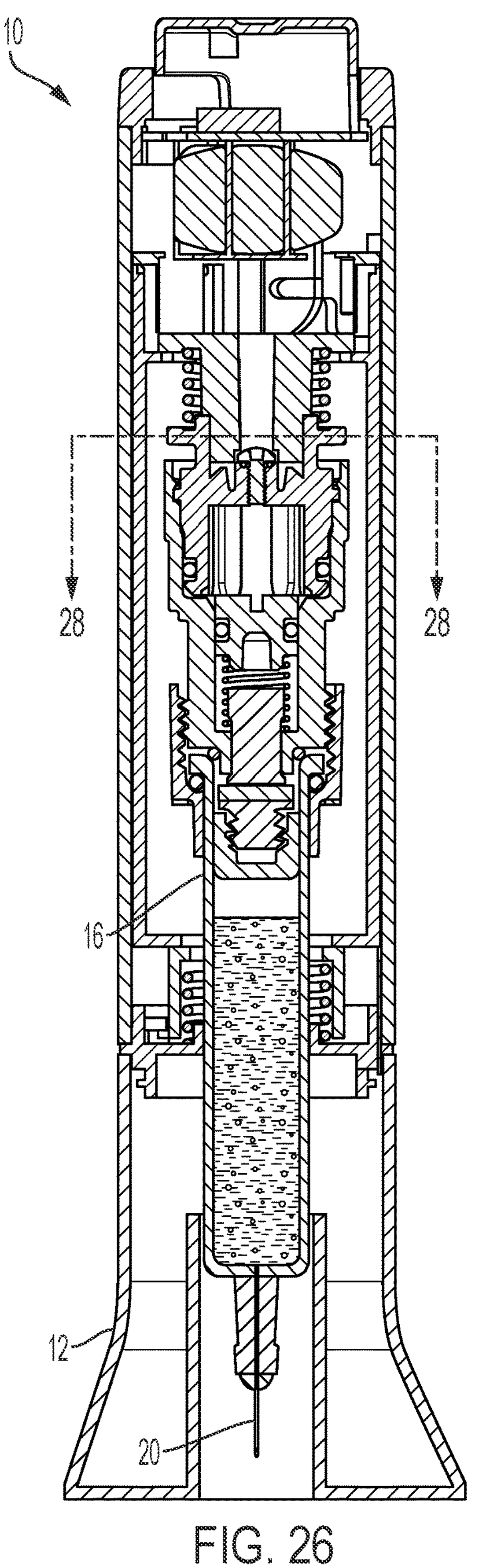
FIG. 26 is a longitudinal sectional view of the therapeutic agent delivery system of FIG. 1 in an initial or first configuration.

Illustratively, actuation of the therapeutic agent delivery system 10 is as follows. Referring to FIG. 26, the therapeutic agent delivery system 10 is illustrated in an initial or first configuration. In the first configuration, the therapeutic agent delivery assembly 16 is disposed in the stowed configuration (illustratively, a configuration in which the needle 20 is disposed entirely within the housing 12).

Figure 27:
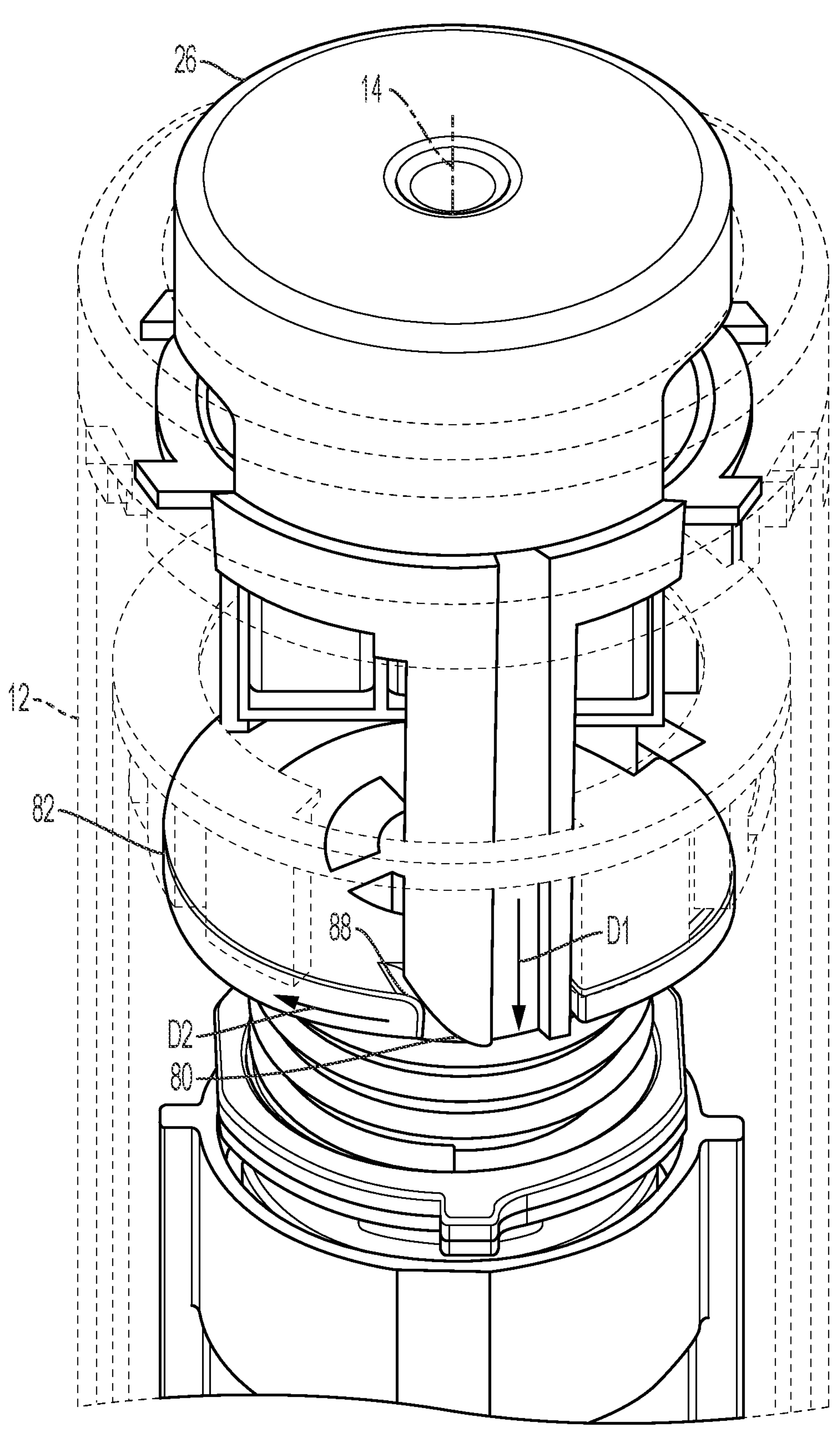
FIG. 27 is a detail top perspective view of a proximal end portion of the therapeutic agent delivery system of FIG. 1 in the first configuration; several external components are shown in hidden lines to illustrate internal components.
Figure 28:
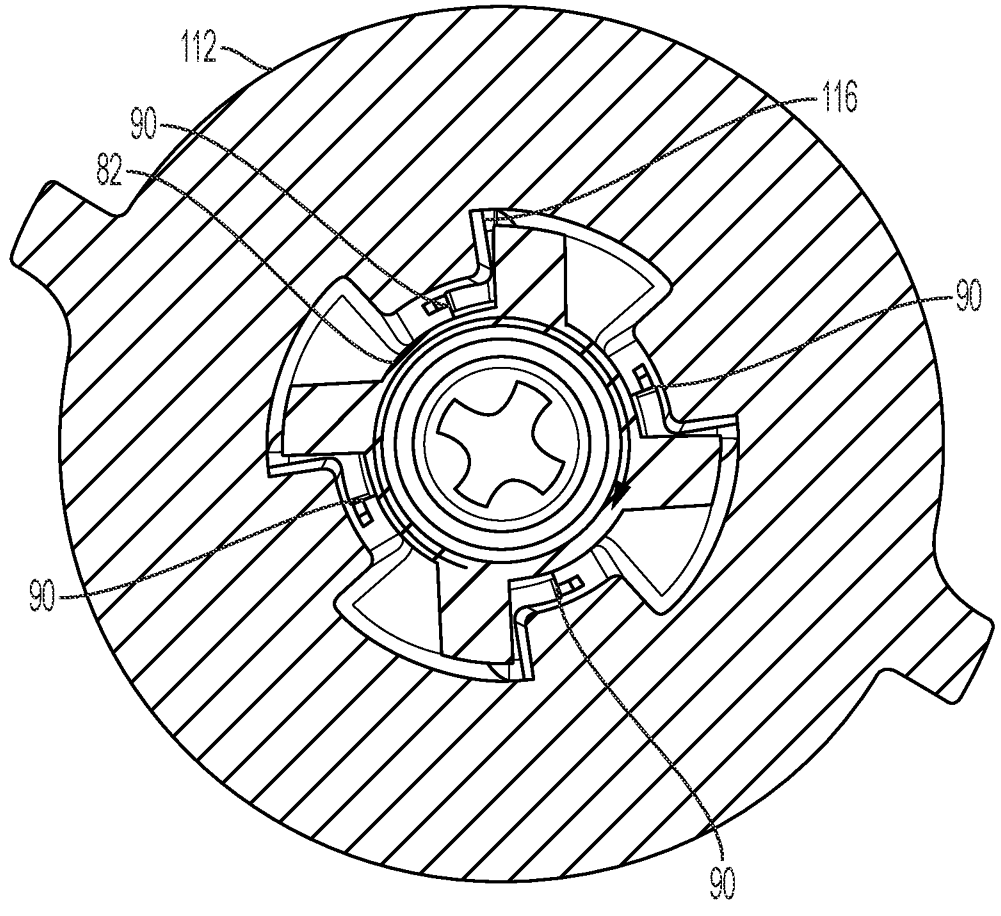
FIG. 28 is a cross sectional view of the therapeutic agent delivery system through an input drive and a shuttle of a pressure generating actuator along line 28-28 of FIG. 27 upon actuating a user input.

Referring to FIG. 27, the user input 26 and the input drive 82 are illustrated in the first configuration. In this configuration, the user input 26 may be actuated by a user to actuate the therapeutic agent delivery system 10. More specifically, the user input 26 may be pressed and translated in a direction D1 (which may be, for example, substantially parallel to the longitudinal axis 14 (that is, parallel±5 degrees)) relative to the housing 12. This action causes the actuation surfaces 80 of the user input 26 (one of which is shown in FIG. 27) to engage the actuation surfaces 88 of the input drive 82 (one of which is shown in FIG. 27). The user input 26 thereby rotates the input drive 82 in a direction D2. As shown in FIG. 28, this action in turn causes the ledges 90 of the input drive 82 to begin to slide over and subsequently disengage the ledges 116 of the shuttle 112.

Figure 29:
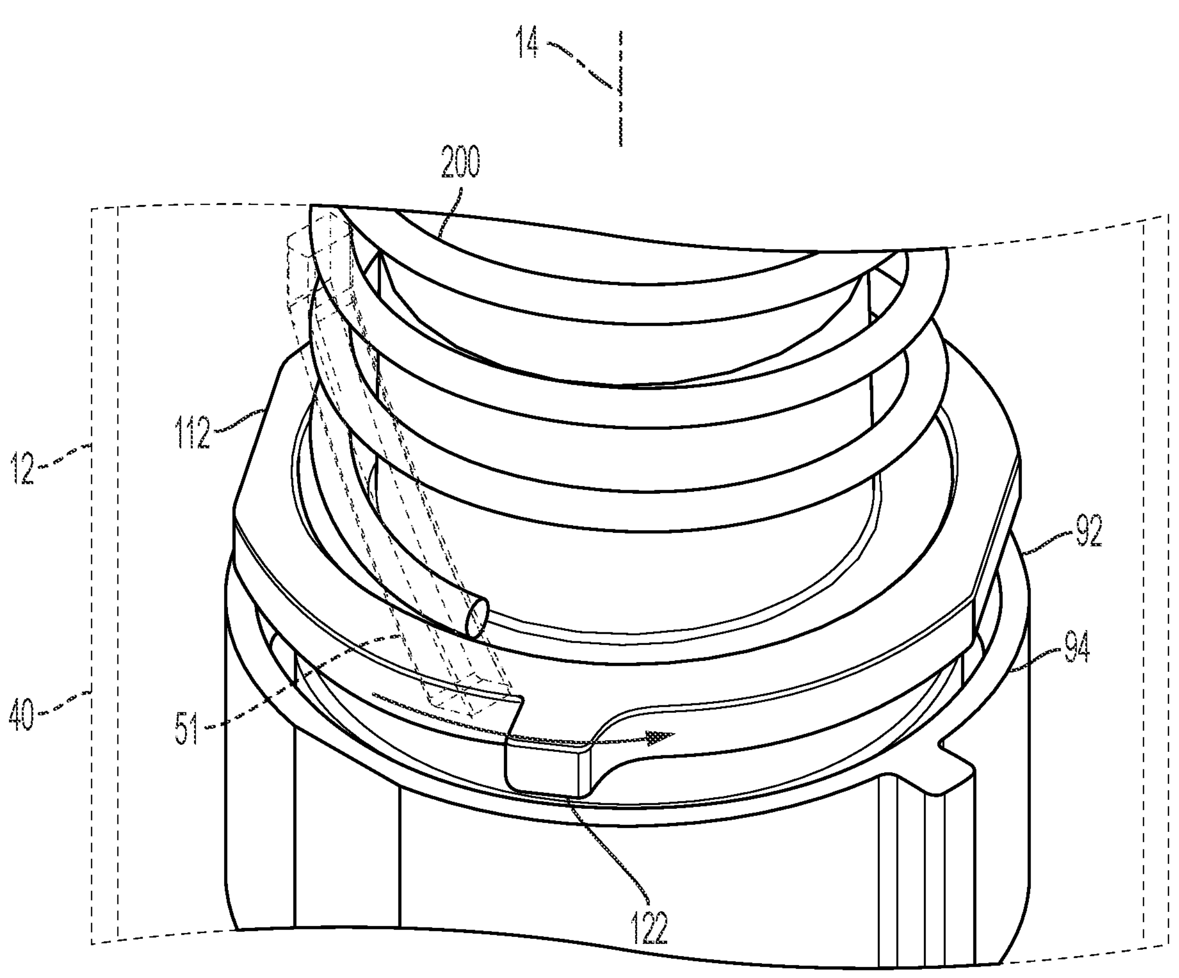
FIG. 29 is a detail top perspective view of the therapeutic agent delivery system of FIG. 1 upon a deployment spring expanding and moving the therapeutic agent delivery assembly distally relative to the housing; several external components are shown in hidden lines to illustrate internal components.
Figure 30:
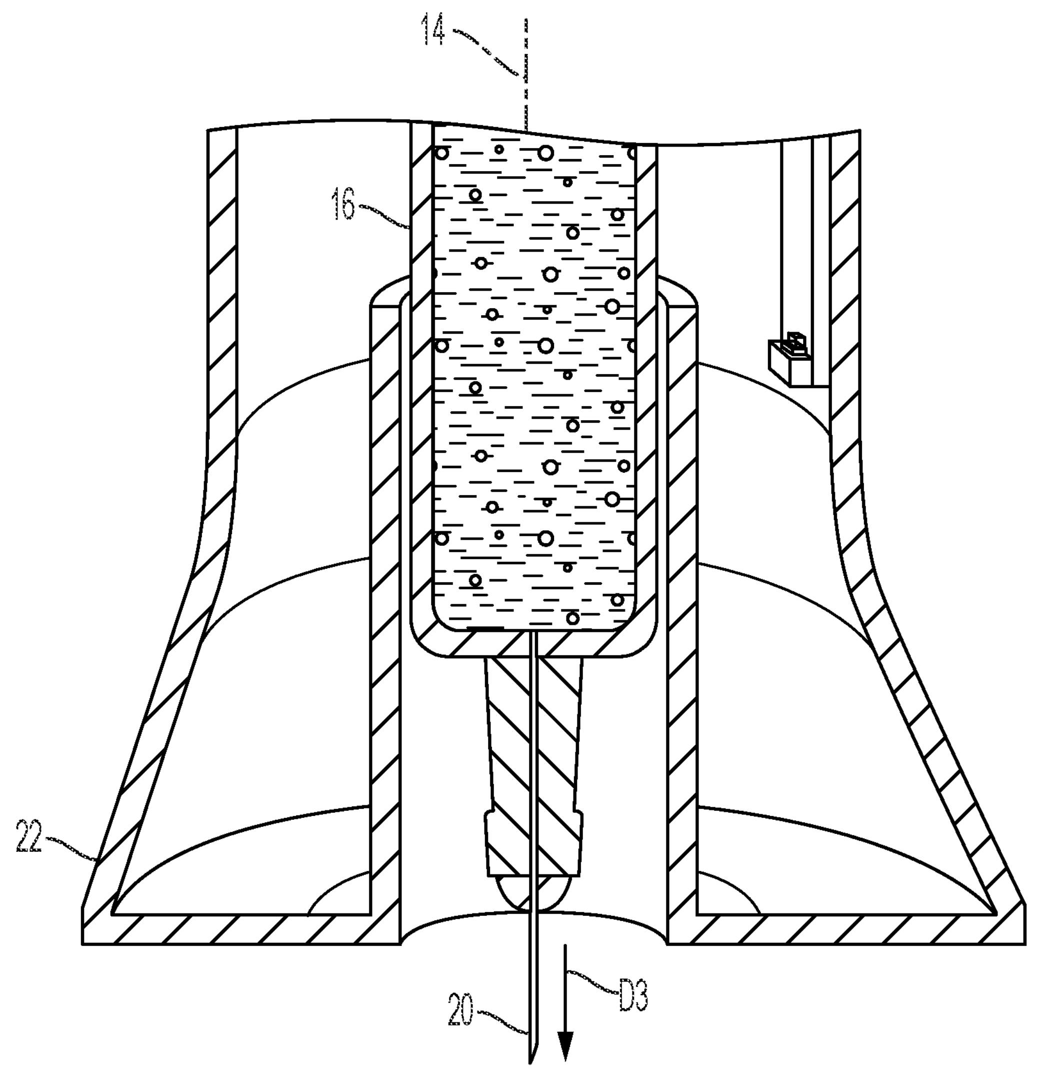
FIG. 30 is a longitudinal sectional partial view of the therapeutic agent delivery system of FIG. 1 upon the therapeutic agent delivery assembly moving to a deployed configuration.

As shown in FIG. 29, a compression spring 200 disposed between the input drive 82 and the shuttle 112 is relatively unconstrained upon disengagement of the input drive 82 and the shuttle 112. As such, the compression spring 200 expands and pushes the therapeutic agent delivery assembly 16 (shown elsewhere) distally relative to the housing 12. As shown in FIG. 30, the therapeutic agent delivery assembly 16 thereby moves from the stowed configuration to the deployed configuration (illustratively, a configuration in which the needle 20 is partially exposed at the distal end portion 22 of the housing 12 and configured to engage the subject and deliver the therapeutic agent to the subject). Illustratively, the needle 20 translates from the stowed configuration to the deployed configuration in a direction D3 that is substantially parallel to the longitudinal axis 14 (that is, parallel±5 degrees).

Figure 31:
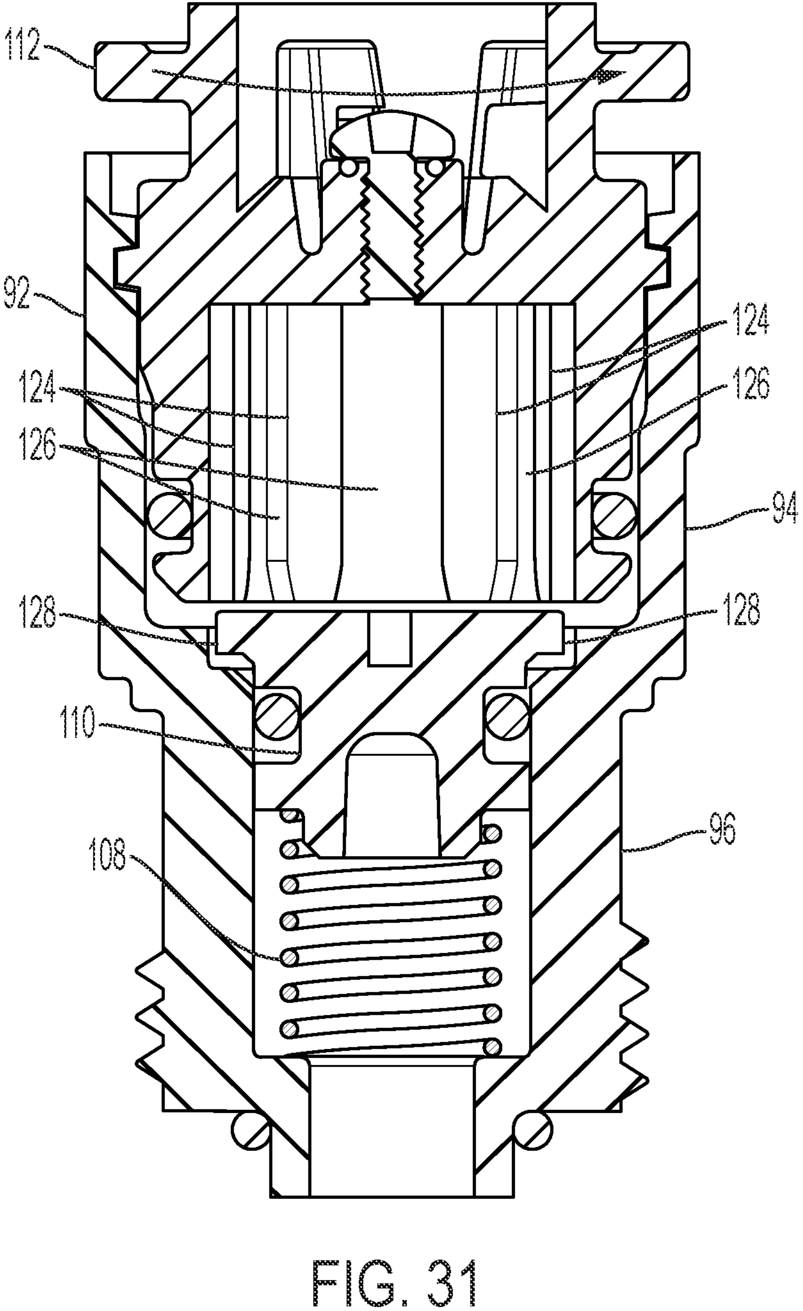
FIG. 31 is a longitudinal sectional view of a shuttle of the pressure generating actuator being rotated relative to first and second mixing chambers of the pressure generating actuator and thereby actuating the actuator.
Figure 32:
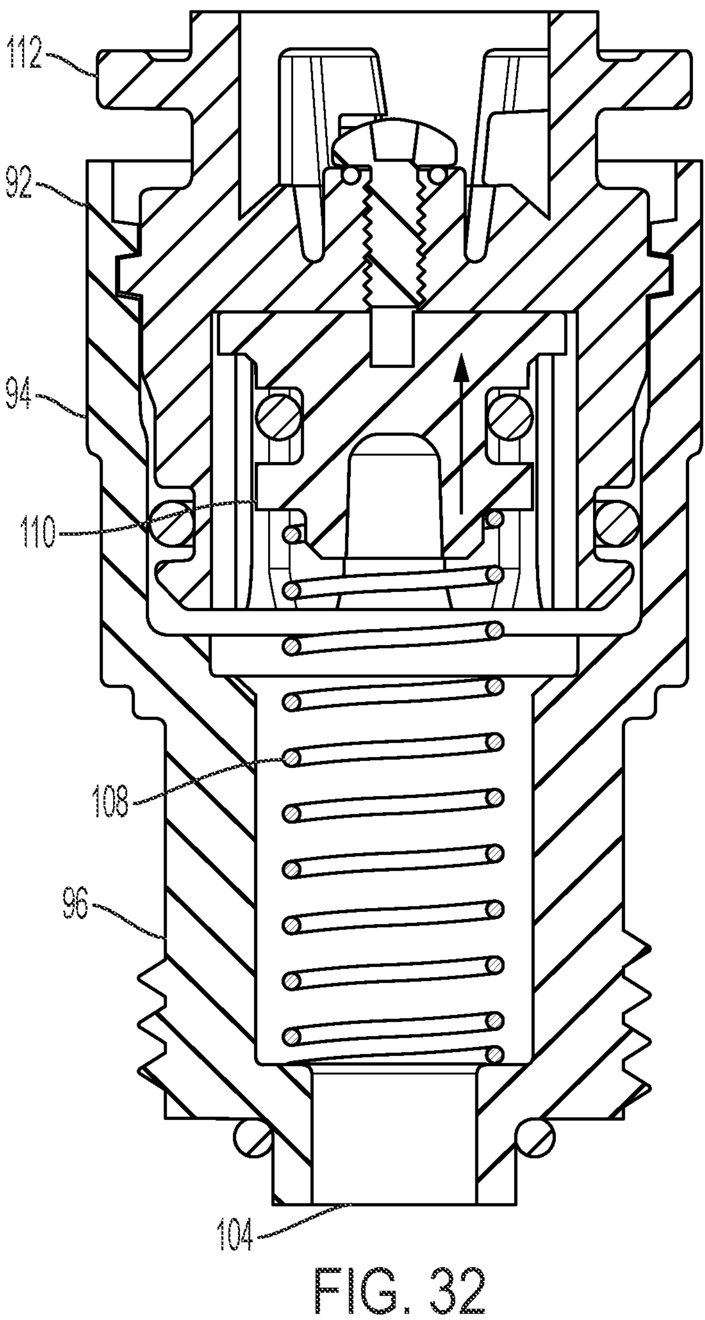
FIG. 32 is a longitudinal sectional view of the shuttle and a mixing piston of the pressure generating actuator in a deployed configuration.

Referring again to FIG. 29, translation of the therapeutic agent delivery assembly 16 distally relative to the housing 12 also causes the radially-outwardly extending fingers 122 of the shuttle 112 (one of which is shown in FIG. 29) to engage and slide over the helically extending ramps 51 (one of which is shown in FIG. 29) of the proximal inner housing portion 40. This engagement causes the shuttle 112 to rotate relative to the mixing chambers 94, 96 of the pressure generating actuator 92 (illustratively, about an axis that is substantially parallel to the longitudinal axis 14 (that is, parallel±5 degrees)), which actuates the pressure generating actuator 92. More specifically and as illustrated in FIG. 31, rotating the shuttle 112 relative to the first and second mixing chambers 94, 96 angularly misaligns the radially-inwardly extending tabs 124 of the shuttle 112 with the radially-outwardly extending tabs 128 of the mixing piston 110 and angularly aligns the channels 126 of the shuttle 112 with the radially-outwardly extending tabs 128 of the mixing piston 110. As a result, the actuator spring 108 is relatively unconstrained and, as shown in FIG. 32, the actuator spring 108 expands and translates the mixing piston 110 into the shuttle 112 and the first mixing chamber 94. The reagents in the first mixing chamber 94 and the second mixing chamber 96 then mix and react to provide a pressurized gas, which the pressure generating actuator 92 delivers from the actuator outlet 104.

Figure 33:
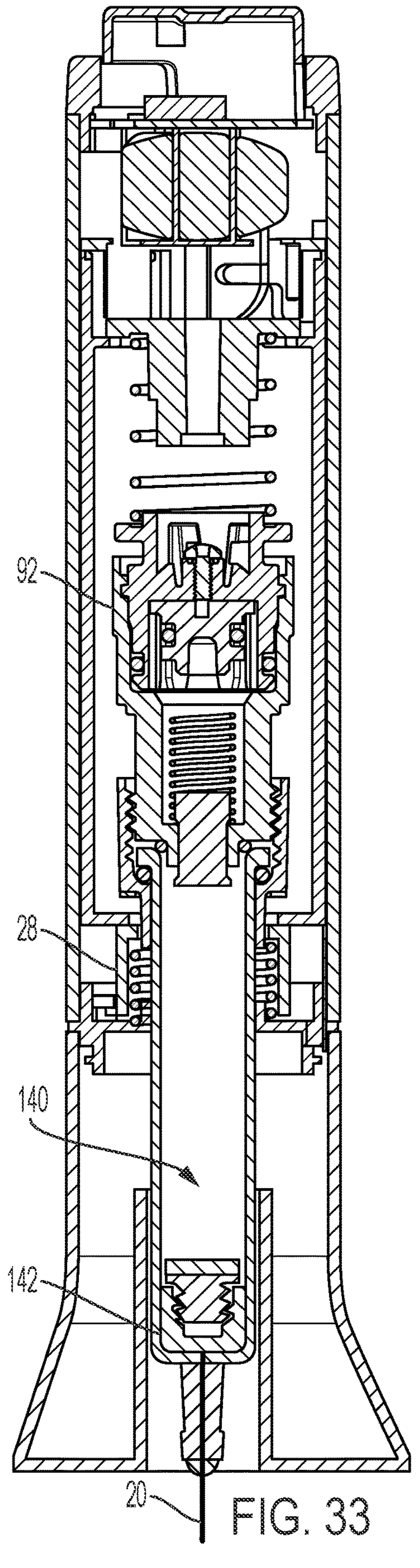
FIG. 33 is a longitudinal sectional view of the therapeutic agent delivery system of FIG. 1 upon a syringe piston moving in a syringe passageway to discharge a therapeutic agent from the needle.
Figure 34:
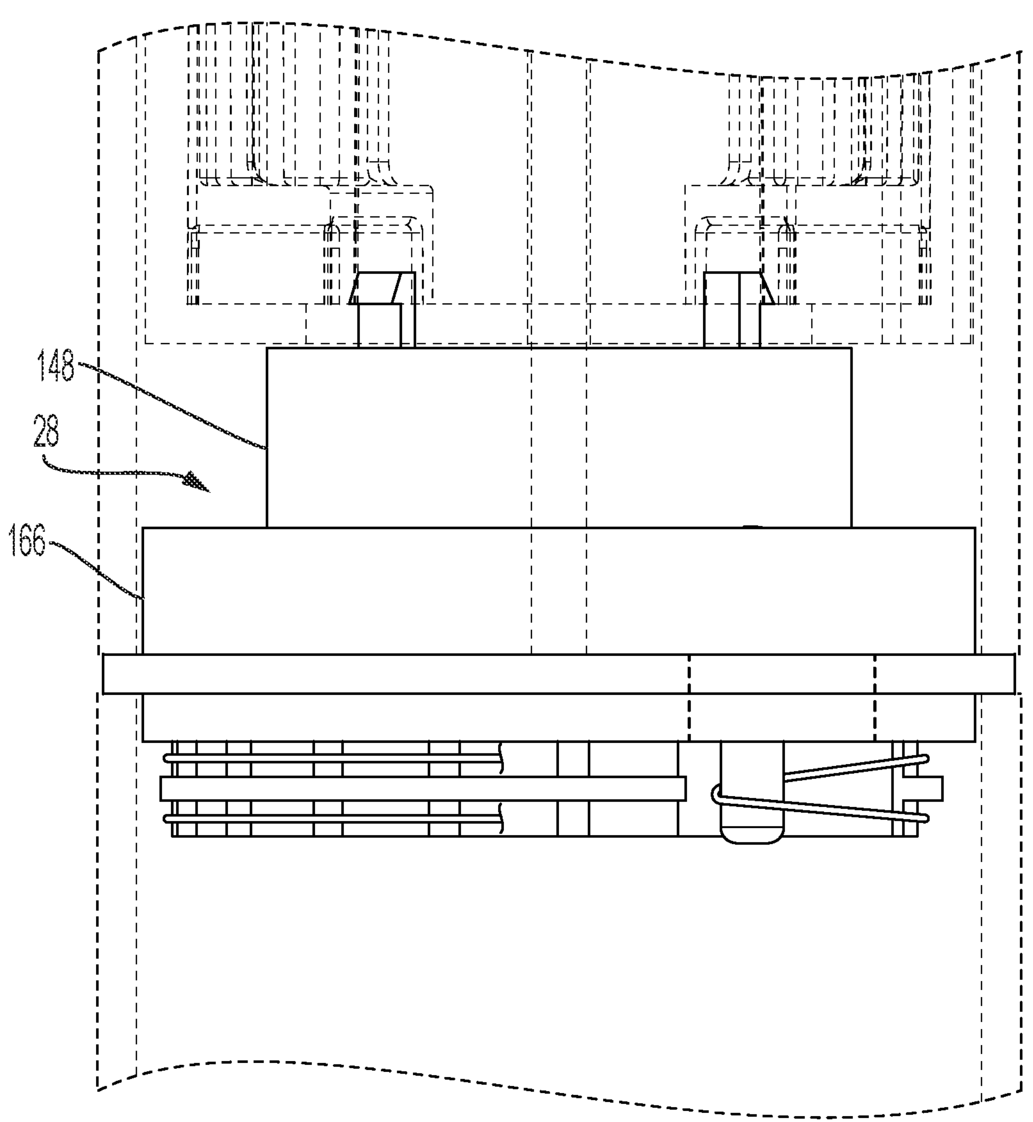
FIG. 34 is a side view of the retraction mechanism of FIG. 25 in an initial or first configuration.
Figure 35:
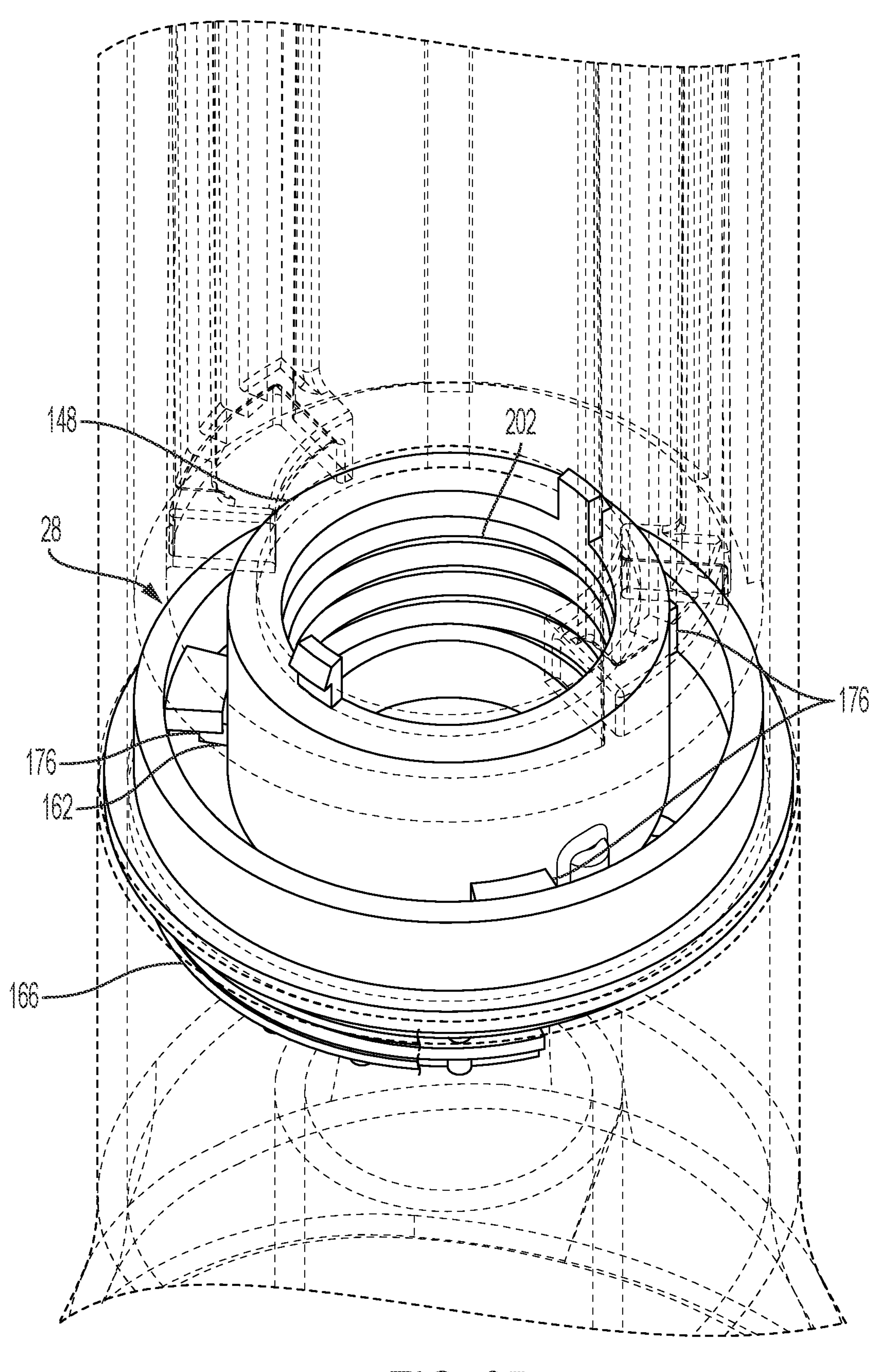
FIG. 35 is a top perspective view of the retraction mechanism of FIG. 25 in the first configuration.
Figure 36:
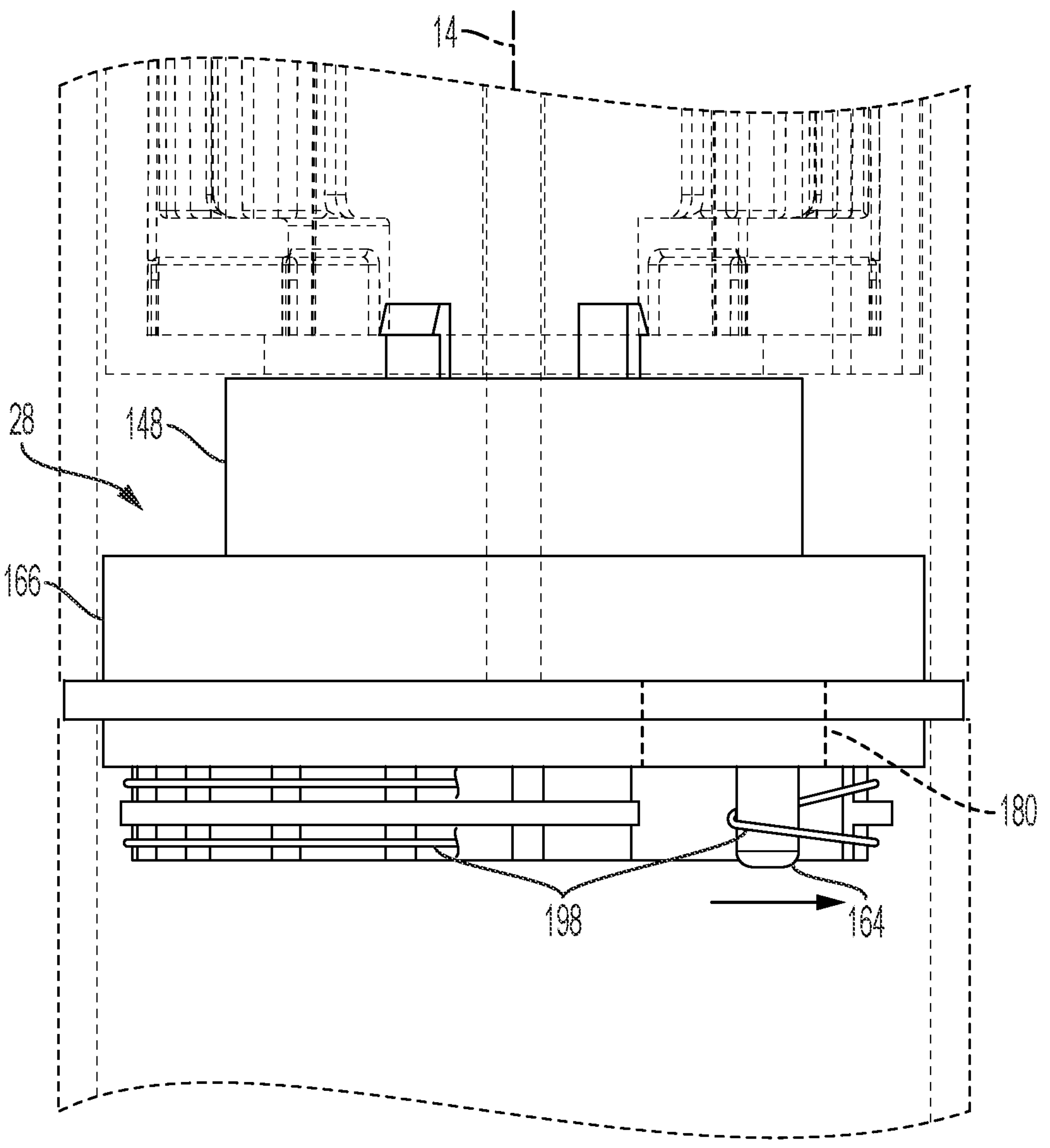
FIG. 36 is a side view of the retraction mechanism of FIG. 25 during actuation.
Figure 37:
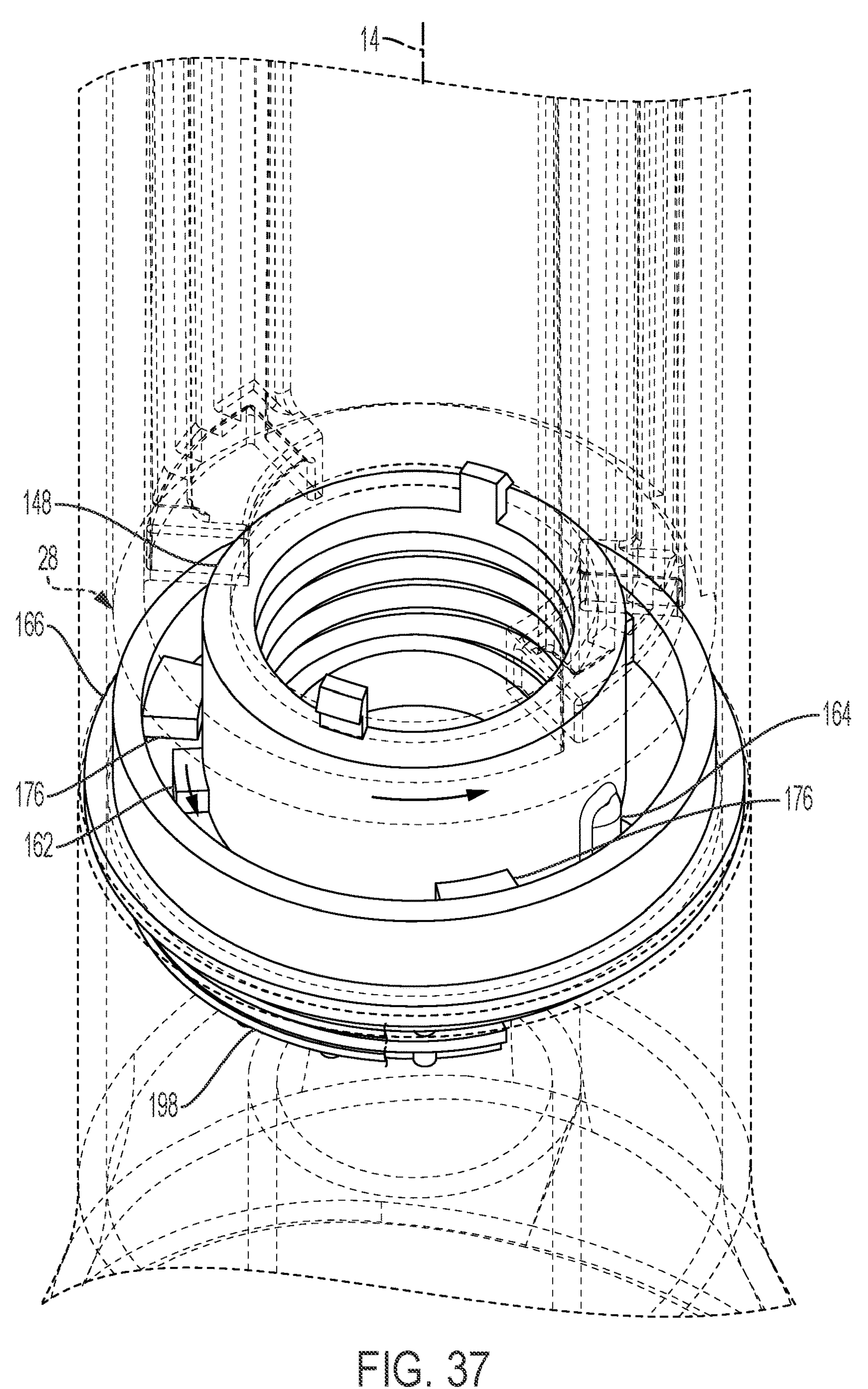
FIG. 37 is a top perspective view of the retraction mechanism of FIG. 25 during actuation.
Figure 38:
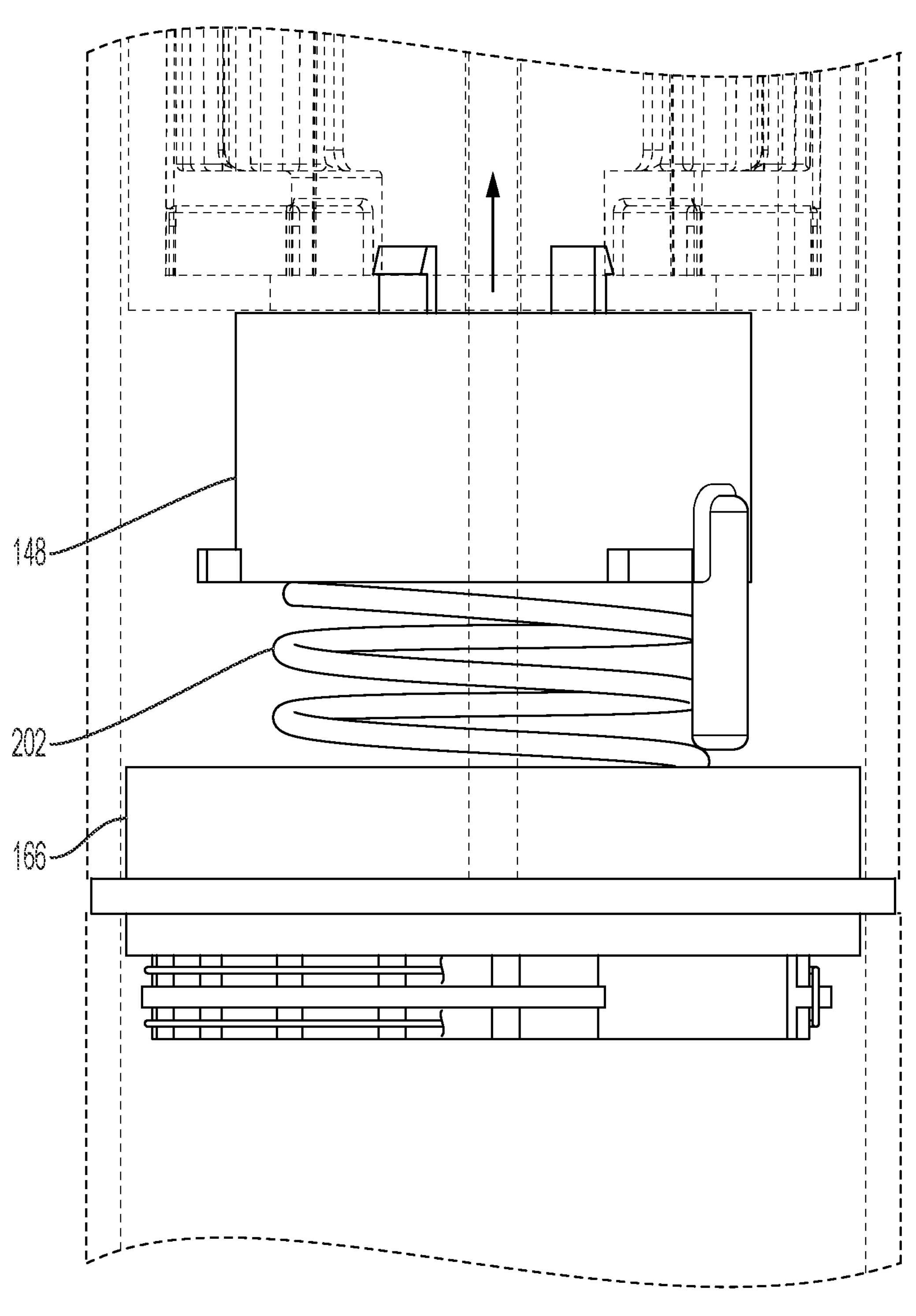
FIG. 38 is a side view of the retraction mechanism of FIG. 25 in an actuated configuration.
Figure 39:
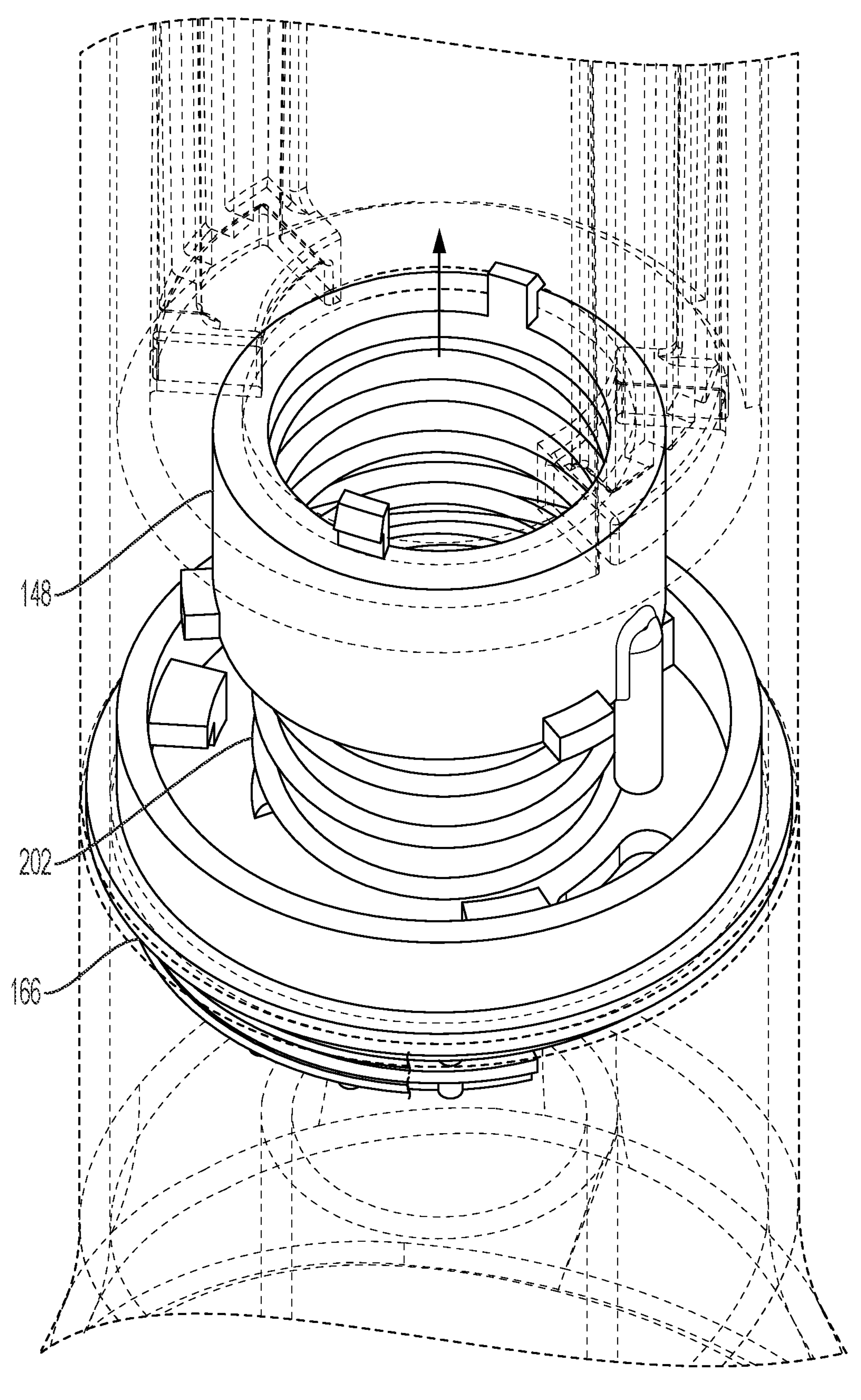
FIG. 39 is a top perspective view of the retraction mechanism of FIG. 25 in the actuated configuration.
Figure 40:
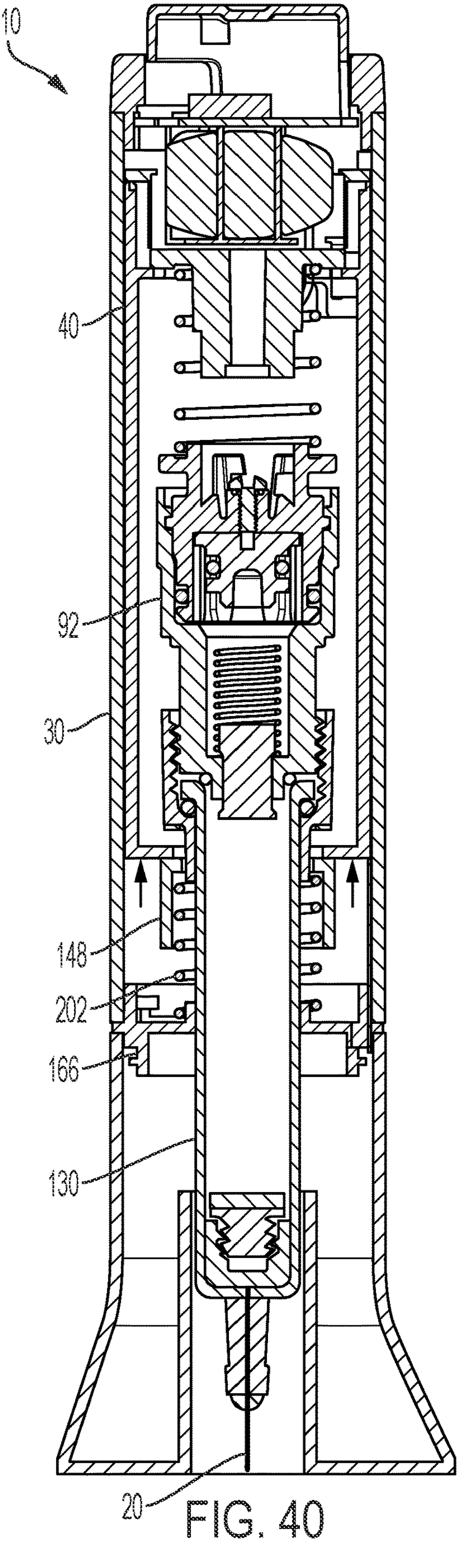
FIG. 40 is a longitudinal sectional view of the therapeutic agent delivery system of FIG. 1 with the needle in a retracted configuration.

Referring to FIG. 33, the pressure generating actuator 92 delivers the pressurized gas to the syringe passageway 140, which translates the syringe piston 142 distally within the syringe passageway 140. As such, the syringe piston 142 pushes the therapeutic fluid distally to the needle 20, and the needle 20 discharges the therapeutic fluid and delivers the therapeutic fluid to the subject. While delivering the therapeutic fluid to the subject and as shown in FIGS. 34 and 35, the retraction mechanism 28 remains in its initial or first configuration. More specifically, the retraction cap 148 is secured to the retraction base 166 via the detachable coupling features (illustratively, the plurality of ledges 162 and 176—see FIG. 35), and a compression spring 202 is carried in a higher energy storage configuration (that is, a loaded or compressed configuration) between the retraction cap 148 and the retraction base 166. After delivering the therapeutic fluid to the subject (illustratively, determined by the sensor 194 sensing that the magnetic component 146, and the syringe piston 142, are disposed near the outlet portion 144 of the syringe assembly 130—all shown elsewhere), the electronics assembly 188 (shown elsewhere) actuates the retraction mechanism 28. More specifically, the electronics assembly 188 delivers an electric current to the wire 198 to heat and, as shown in FIGS. 36 and 37, thereby contract the wire 198. The wire 198 thereby pulls and slides the post 164 of the retraction cap 148 in the opening 180 of the retraction base 166, which causes the retraction cap 148 to rotate relative to the retraction base 166 about the longitudinal axis 14. Upon such rotation, the coupling features of the retraction cap 148 (illustratively, the plurality of ledges 162) disengage the coupling features of the retraction base 166 (illustratively, the plurality of ledges 176). As shown in FIGS. 38 and 39, the spring 202 is then relatively unconstrained, and the spring 202 releases stored energy to reconfigure from the higher energy storage configuration to a lower energy storage configuration (that is, the spring 202 expands). The spring 202 thereby urges the retraction cap 148 away from the retraction base 166, which, as shown in FIG. 40, translates the proximal inner housing portion 40, the pressure generating actuator 92, and the syringe assembly 130 proximally relative to the proximal outer housing portion 30. This action causes the needle 20 to translate from the deployed configuration to the retracted configuration. Illustratively, the therapeutic agent delivery system 10 cannot be actuated again (that is, the therapeutic agent delivery system 10 may be "locked out), and the therapeutic agent delivery system 10 may be discarded.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A therapeutic agent delivery system, comprising:

an elongated housing having a proximal end portion, a distal end portion, and a longitudinal axis extending between the proximal end portion and the distal end portion;

a therapeutic agent delivery assembly carried by the housing, the therapeutic agent delivery assembly comprising:

a chamber comprising a passageway configured to carry a therapeutic agent;

a needle in communication with the passageway;

the therapeutic agent delivery assembly being translatable relative to the housing along the longitudinal axis from a stowed configuration to a deployed configuration, in the deployed configuration the needle at least partially extending distally from the distal end portion of the housing, and the therapeutic agent delivery assembly being translatable relative to the housing from the deployed configuration to a retracted configuration, in the retracted configuration the needle being disposed proximally relative to the distal end portion of the housing;

a user input at the proximal end portion configured to be actuated by a user, actuation of the user input translating the therapeutic agent delivery assembly from the stowed configuration to the deployed configuration; and a retraction mechanism comprising:

a retraction base;

a retraction cap carried by the retraction base and being rotatable relative to the retraction base;

a biasing element carried between the retraction base and the retraction cap and being reconfigurable from a higher energy storage configuration to a lower energy storage configuration to translate the retraction cap, the chamber, and the needle together relative to the retraction base;

an electronics assembly configured to generate a retraction signal; and a wire coupled to at least one of the retraction base and the retraction cap and being actuatable by the electronics assembly in response to the retraction signal to permit the biasing element to reconfigure from the higher energy storage configuration to the lower energy storage configuration, the biasing element thereby translating the therapeutic agent delivery assembly from the deployed configuration to the retracted configuration, wherein the wire comprises a shape memory material configured to contract upon receiving thermal energy from the electronics assembly, wherein contracting the wire rotates the retraction cap relative to the retraction base to disengage coupling features of the retraction cap and the retraction base.

2. The therapeutic agent delivery system of claim 1, wherein the biasing element comprises a compression spring, the higher energy storage configuration is a compressed configuration, and the lower energy storage configuration is an expanded configuration.

3. The therapeutic agent delivery system of claim 1, wherein the electronics assembly includes a heating element configured to provide thermal energy to the wire to contract the wire in response to the retraction signal.

4. The therapeutic agent delivery system of claim 3, wherein the electronics assembly comprises a sensor configured to sense discharge of the therapeutic agent from the needle, and the electronics assembly being configured to send the retraction signal upon the sensor sensing discharge of the therapeutic agent from the needle.

5. The therapeutic agent delivery system of claim 1, wherein the wire is operably coupled to the electronics assembly, and the retraction signal comprises an electric current, and wherein the wire is actuated by contracting upon receiving the electric current.

6. The therapeutic agent delivery system of claim 1, wherein one of the retraction cap and the retraction base includes a post and the other of the retraction cap and the retraction base includes an opening, the wire is coupled to the post, and when actuated the wire pulls the post such that the post slides within the opening.

7. The therapeutic agent delivery system of claim 1, wherein the housing further comprises:

an outer housing; and an inner housing translatably carried within the outer housing, the inner housing translatably carrying the therapeutic agent delivery assembly;

wherein the therapeutic agent delivery assembly translates relative to the inner housing and the outer housing when translating from the stowed configuration to the deployed configuration, and the therapeutic agent delivery assembly translates together with the inner housing relative to the outer housing from the deployed configuration to the retracted configuration.

8. The therapeutic agent delivery system of claim 7, wherein a proximal end portion of the retraction cap includes a coupling feature for coupling the retraction cap to the inner housing when the therapeutic agent delivery assembly is in the deployed configuration.

9. The therapeutic agent delivery system of claim 1, wherein the retraction base includes a main body having a generally annular shape and including a recess at a proximal end portion that receives the retraction cap and the biasing element.

10. The therapeutic agent delivery system of claim 1, further comprising the therapeutic agent contained in the chamber, wherein the therapeutic agent comprises a combined GIP/GLP-1 agonist.

11. The therapeutic agent delivery system of claim 10, wherein the therapeutic agent comprises tirzepatide.

12. The therapeutic agent delivery system of claim 1, wherein the electronics assembly is positioned at the proximal end portion of the elongated housing.

* * * * *